United States Patent
Zhang et al.

(10) Patent No.: US 11,746,328 B2
(45) Date of Patent: Sep. 5, 2023

(54) METHODS AND SYSTEMS FOR FUNCTIONAL MATURATION OF IPSC AND ESC DERIVED CARDIOMYOCYTES

(71) Applicant: Agilent Technologies, Inc., Santa Clara, CA (US)

(72) Inventors: Xiaoyu Zhang, San Diego, CA (US); Yama A. Abassi, San Diego, CA (US); Nan Li, San Diego, CA (US); Xiaobo Wang, San Diego, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 676 days.

(21) Appl. No.: 16/490,302

(22) PCT Filed: Mar. 3, 2018

(86) PCT No.: PCT/US2018/020817
§ 371 (c)(1),
(2) Date: Aug. 30, 2019

(87) PCT Pub. No.: WO2018/161063
PCT Pub. Date: Sep. 7, 2018

(65) Prior Publication Data
US 2020/0071672 A1 Mar. 5, 2020

Related U.S. Application Data

(60) Provisional application No. 62/490,505, filed on Apr. 26, 2017, provisional application No. 62/466,992, filed on Mar. 3, 2017.

(51) Int. Cl.
| | | |
|---|---|---|
| *C12N 5/077* | (2010.01) | |
| *C12N 5/00* | (2006.01) | |
| *C12N 5/074* | (2010.01) | |
| *C12N 13/00* | (2006.01) | |
| *G01N 27/02* | (2006.01) | |

(52) U.S. Cl.
CPC ......... *C12N 5/0657* (2013.01); *C12N 5/0018* (2013.01); *C12N 5/0696* (2013.01); *C12N 13/00* (2013.01); *G01N 27/028* (2013.01); *C12N 2506/45* (2013.01); *C12N 2529/00* (2013.01)

(58) Field of Classification Search
CPC .. C12N 5/0657; C12N 5/0018; C12N 5/0696; C12N 13/00; C12N 2506/45; C12N 2529/00; G01N 27/028; A61K 35/545; A61K 35/34
See application file for complete search history.

(56) References Cited

U.S. PATENT DOCUMENTS

| | | |
|---|---|---|
| 2,656,508 A | 10/1953 | Coulter |
| 3,259,842 A | 7/1966 | Coulter et al. |
| 3,743,581 A | 7/1973 | Cady et al. |
| 3,890,201 A | 6/1975 | Cady |
| 4,072,578 A | 2/1978 | Cady et al. |
| 4,225,410 A | 9/1980 | Pace |
| 4,559,310 A | 12/1985 | Cantor et al. |
| 4,686,190 A | 8/1987 | Cramer et al. |
| 4,920,047 A | 4/1990 | Giaever et al. |
| 5,001,048 A | 3/1991 | Taylor et al. |
| 5,134,070 A | 7/1992 | Casnig |
| 5,187,096 A | 2/1993 | Giaever et al. |
| 5,218,312 A | 6/1993 | Moro |
| 5,247,827 A | 9/1993 | Shah |
| 5,278,048 A | 1/1994 | Parce et al. |
| 5,284,753 A | 2/1994 | Goodwin, Jr. |
| 5,514,555 A | 5/1996 | Springer et al. |
| 5,563,067 A | 10/1996 | Sugihara et al. |
| 5,601,997 A | 2/1997 | Tchao |
| 5,622,872 A | 4/1997 | Ribi |
| 5,626,734 A | 5/1997 | Docoslis et al. |
| 5,643,742 A | 7/1997 | Malin et al. |
| 5,725,563 A | 3/1998 | Klotz |
| 5,766,934 A | 6/1998 | Guiseppi-Elie |
| 5,800,467 A | 9/1998 | Park et al. |
| 5,801,055 A | 9/1998 | Henderson |
| 5,810,725 A | 9/1998 | Sugihara et al. |
| 5,824,494 A | 10/1998 | Feldberg |
| 5,851,489 A | 12/1998 | Wolf et al. |
| 5,981,268 A | 11/1999 | Kovacs et al. |
| 6,033,628 A | 3/2000 | Kaltenback et al. |
| 6,051,422 A | 4/2000 | Kovacs et al. |
| 6,132,683 A | 10/2000 | Sugihara et al. |
| 6,169,394 B1 | 1/2001 | Frazier et al. |

(Continued)

FOREIGN PATENT DOCUMENTS

| | | |
|---|---|---|
| CN | 1671860 A | 9/2005 |
| EP | 1138758 A1 | 10/2001 |

(Continued)

OTHER PUBLICATIONS

Sun et al. "Biowire platform for maturation of human pluripotent stem cell-derived cardiomyocytes." Methods vol. 101, May 15, 2016, pp. 21-26 (Year: 2016).*

Lamore et al. "Cellular impedance assays for predictive preclinical drug screening of kinase inhibitor cardiovascular toxicity." Toxicol Sci. Oct. 2013;135(2):402-13. (Year: 2013).*

Riedel et al. ""Functional and pharmacological analysis of cardiomyocytes differentiated from human peripheral blood mononuclear-derived pluripotent stem cells.Stem Cell Reports. May 29, 2014;3(1):131-41. (Year: 2014).*

"xCELLigence RTCA CardioECR—Cardiomyocyte Contractility & Electrical Activity." https://www.agilent.com/en/product/cell-analysis/real-time-cell-analysis/rtca-analyzers/xcelligence-rtca-cardioecr-cardiomyocyte-contractility-electrical-activity-741225. Retrieved Oct. 12, 2022 (Year: 2022).*

(Continued)

*Primary Examiner* — Titilayo Moloye

(57) ABSTRACT

Methods of inducing functional maturation of immature cardiomyocytes derived from induced pluripotent stem cells (iPSCs) and embryonic stem cells (ESCs) by electrically pacing the immature cardiomyocytes according to a pulse profile that induces maturation until the immature cardiomyocytes mature into functionally adult cardiomyocytes.

5 Claims, 11 Drawing Sheets

(56) References Cited

U.S. PATENT DOCUMENTS

| | | |
|---|---|---|
| 6,232,062 B1 | 5/2001 | Kayyem et al. |
| 6,235,520 B1 | 5/2001 | Malin et al. |
| 6,280,586 B1 | 8/2001 | Wolf et al. |
| 6,288,527 B1 | 9/2001 | Sugihara et al. |
| 6,368,795 B1 | 4/2002 | Hefti et al. |
| 6,368,851 B1 | 4/2002 | Baumann et al. |
| 6,376,233 B1 | 4/2002 | Wolf et al. |
| 6,377,057 B1 | 4/2002 | Borkholder et al. |
| 6,440,662 B1 | 8/2002 | Van Gerwen et al. |
| 6,448,030 B1 | 9/2002 | Rust et al. |
| 6,448,794 B1 | 9/2002 | Cheng et al. |
| 6,461,808 B1 | 10/2002 | Bodner et al. |
| 6,472,144 B2 | 10/2002 | Malin et al. |
| 6,485,905 B2 | 11/2002 | Hefti |
| 6,492,175 B1 | 12/2002 | Mueller et al. |
| RE37,977 E | 2/2003 | Sugihara et al. |
| 6,535,822 B2 | 3/2003 | Mansky et al. |
| 6,566,079 B2 | 5/2003 | Hefti |
| 6,573,063 B2 | 6/2003 | Hochman |
| 6,596,499 B2 | 7/2003 | Jalink |
| 6,626,902 B1 | 9/2003 | Kucharczyk et al. |
| 6,627,461 B2 | 9/2003 | Chapman et al. |
| 6,630,359 B1 | 10/2003 | Caillat et al. |
| 6,637,257 B2 | 10/2003 | Sparks |
| 6,638,743 B2 | 10/2003 | Baumann et al. |
| RE38,323 E | 11/2003 | Sugihara et al. |
| 6,649,402 B2 | 11/2003 | Van der Weide et al. |
| 6,686,193 B2 | 2/2004 | Maher et al. |
| 6,716,620 B2 | 4/2004 | Bashir et al. |
| 6,723,523 B2 | 4/2004 | Lynes et al. |
| 6,803,229 B2 | 10/2004 | Martin et al. |
| 6,835,552 B2 | 12/2004 | Miles et al. |
| 6,846,639 B2 | 1/2005 | Miles et al. |
| 6,852,525 B1 | 2/2005 | Cantor |
| 6,998,249 B1 | 2/2006 | McKim et al. |
| 7,010,347 B2 | 3/2006 | Schecter |
| 7,148,059 B1 | 12/2006 | Tillotson et al. |
| 7,192,752 B2 | 3/2007 | Xu et al. |
| 7,208,279 B2 | 4/2007 | Gilchrist et al. |
| 7,294,334 B1 | 11/2007 | Michal et al. |
| 7,399,631 B2 | 7/2008 | Giaever et al. |
| 7,459,303 B2 | 12/2008 | Wang et al. |
| 7,468,255 B2 | 12/2008 | Xu et al. |
| 7,470,533 B2 | 12/2008 | Xu et al. |
| 7,476,827 B1 | 1/2009 | Bhullar et al. |
| 7,510,699 B2 | 3/2009 | Black et al. |
| 7,553,448 B2 | 6/2009 | Kumar et al. |
| 7,560,269 B2 | 7/2009 | Wang et al. |
| 7,732,127 B2 | 6/2010 | Wang et al. |
| 7,842,246 B2 | 11/2010 | Wohlstadter et al. |
| 7,876,108 B2 | 1/2011 | Abassi et al. |
| 8,026,080 B2 | 9/2011 | Wang et al. |
| 8,041,515 B2 | 10/2011 | Wang et al. |
| 8,206,903 B2 | 6/2012 | Wang et al. |
| 8,263,375 B2 | 9/2012 | Abassi et al. |
| 8,344,742 B2 | 1/2013 | Abassi et al. |
| 8,420,363 B2 | 4/2013 | Wang et al. |
| 8,916,357 B2 | 12/2014 | Abassi et al. |
| 8,921,041 B2 | 12/2014 | Wang et al. |
| 9,399,787 B2 | 7/2016 | Abassi et al. |
| 9,612,234 B2 | 4/2017 | Li et al. |
| 9,625,472 B2 | 4/2017 | Xu et al. |
| 9,709,548 B2 | 7/2017 | Wang et al. |
| 10,012,636 B2 | 7/2018 | Wang et al. |
| 10,067,121 B2 | 9/2018 | Abassi et al. |
| 10,533,985 B2 | 1/2020 | Wang et al. |
| 2002/0010492 A1 | 1/2002 | Donovan et al. |
| 2002/0032531 A1 | 3/2002 | Mansky et al. |
| 2002/0076690 A1 | 6/2002 | Miles et al. |
| 2002/0086280 A1 | 7/2002 | Lynes et al. |
| 2002/0090649 A1 | 7/2002 | Chan et al. |
| 2002/0110847 A1 | 8/2002 | Baumann et al. |
| 2002/0150886 A1 | 10/2002 | Miles et al. |
| 2003/0032000 A1 | 2/2003 | Liu et al. |
| 2003/0072549 A1 | 4/2003 | Facer et al. |
| 2003/0104512 A1 | 6/2003 | Freeman et al. |
| 2003/0116447 A1 | 6/2003 | Surridge et al. |
| 2003/0143625 A1 | 7/2003 | Martin et al. |
| 2003/0157587 A1 | 8/2003 | Gomez et al. |
| 2003/0166015 A1 | 9/2003 | Zarowitz et al. |
| 2003/0211500 A1 | 11/2003 | Woosley |
| 2004/0091397 A1 | 5/2004 | Picard |
| 2004/0106095 A1 | 6/2004 | Thomson et al. |
| 2004/0146849 A1 | 7/2004 | Huang et al. |
| 2004/0152067 A1 | 8/2004 | Wang et al. |
| 2005/0014130 A1 | 1/2005 | Liu et al. |
| 2005/0153425 A1 | 7/2005 | Xu et al. |
| 2005/0182447 A1 | 8/2005 | Schecter |
| 2005/0287065 A1 | 12/2005 | Suddarth et al. |
| 2006/0023559 A1 | 2/2006 | Xu et al. |
| 2006/0050596 A1 | 3/2006 | Abassi et al. |
| 2006/0057771 A1 | 3/2006 | Kovacs et al. |
| 2006/0121446 A1 | 6/2006 | Abassi et al. |
| 2006/0161073 A1 | 7/2006 | Singer |
| 2006/0216203 A1 | 9/2006 | Fuller et al. |
| 2006/0240490 A1 | 10/2006 | Lee |
| 2006/0252054 A1 | 11/2006 | Lin et al. |
| 2007/0042347 A1 | 2/2007 | Rosen et al. |
| 2007/0087333 A1 | 4/2007 | Gruters et al. |
| 2007/0172939 A1 | 7/2007 | Xu et al. |
| 2007/0212423 A1 | 9/2007 | Epstein et al. |
| 2007/0281908 A1 | 12/2007 | Liang et al. |
| 2008/0190783 A1 | 8/2008 | Hyland |
| 2008/0286750 A1 | 11/2008 | Xu et al. |
| 2009/0017465 A1 | 1/2009 | Xu |
| 2009/0142790 A1 | 6/2009 | Fang et al. |
| 2009/0155821 A1 | 6/2009 | Kunich et al. |
| 2009/0241698 A1 | 10/2009 | Biksacky |
| 2009/0325213 A1 | 12/2009 | Gambari et al. |
| 2010/0029506 A1 | 2/2010 | Wang et al. |
| 2011/0039294 A1 | 2/2011 | Wang et al. |
| 2011/0231103 A1 | 9/2011 | Fang |
| 2011/0300569 A1 | 12/2011 | Li et al. |
| 2012/0142031 A1 | 6/2012 | Xu et al. |
| 2012/0295253 A1 | 11/2012 | Abassi et al. |
| 2012/0322050 A1 | 12/2012 | Abassi et al. |
| 2013/0123136 A1 | 5/2013 | Abassi et al. |
| 2014/0203818 A1 | 7/2014 | Wang et al. |
| 2015/0125894 A1 | 5/2015 | Laing et al. |
| 2015/0185206 A1 | 7/2015 | Abassi et al. |
| 2015/0218549 A1 | 8/2015 | Li et al. |
| 2015/0231634 A1 | 8/2015 | Szita et al. |
| 2016/0201035 A1 | 4/2016 | Wang et al. |
| 2017/0205391 A1 | 7/2017 | Li et al. |
| 2017/0269062 A1 | 9/2017 | Abassi et al. |
| 2017/0315131 A1 | 11/2017 | Xu et al. |
| 2017/0370907 A1 | 12/2017 | Abassi et al. |
| 2018/0246079 A1 | 8/2018 | Wang et al. |
| 2019/0195861 A1 | 6/2019 | Abassi et al. |

FOREIGN PATENT DOCUMENTS

| | | |
|---|---|---|
| EP | 1195432 B1 | 6/2004 |
| EP | 1040345 B1 | 3/2006 |
| EP | 2213721 | 8/2010 |
| EP | 2291645 | 9/2015 |
| WO | 1996/001836 A1 | 1/1996 |
| WO | 1999/066329 A1 | 12/1999 |
| WO | 2000/037628 A1 | 6/2000 |
| WO | 2000/070343 A2 | 11/2000 |
| WO | 2000/071669 A1 | 11/2000 |
| WO | 2001/025769 A3 | 4/2001 |
| WO | 2001/038873 A3 | 5/2001 |
| WO | 2001/079529 A1 | 10/2001 |
| WO | 2002/004943 A3 | 1/2002 |
| WO | 2002/042766 A3 | 5/2002 |
| WO | 2003/016887 A3 | 2/2003 |
| WO | 2004/010103 A2 | 1/2004 |
| WO | 2004011603 A2 | 2/2004 |
| WO | 2005/005979 A1 | 1/2005 |
| WO | 2005/047482 A2 | 5/2005 |
| WO | 2005/077104 A2 | 8/2005 |
| WO | 2006/017762 A2 | 2/2006 |
| WO | 2006051387 A2 | 2/2006 |

(56) References Cited

FOREIGN PATENT DOCUMENTS

| WO | 2006051387 A1 | 5/2006 | | |
|---|---|---|---|---|
| WO | 2009/137440 A1 | 11/2009 | | |
| WO | 2010/129725 A1 | 11/2010 | | |
| WO | 2011/146531 A1 | 11/2011 | | |
| WO | 2012/043820 A1 | 4/2012 | | |
| WO | 2014/085727 A1 | 6/2014 | | |
| WO | 2015061907 A1 | 5/2015 | | |
| WO | WO-2015061907 A1 * | 5/2015 | ............ | C12M 1/34 |
| WO | 2016/183143 A1 | 11/2016 | | |
| WO | 2017/068421 A1 | 4/2017 | | |
| WO | 2017/087945 A1 | 5/2017 | | |

OTHER PUBLICATIONS

PCT/US2018/020817 International Search Report and Written Opinion dated May 7, 2018.

Baumann et al., "Microelectronic Sensor System for Microphysiological Application on Living Cells", Sensors and Actuators,1999:77-89.

Becker et al. "Separation of Human Breast Cancer Cells from Blood by Differential Dielectric Affinity." Cell Biology, 1995, 92:860-864.

Berens et al. "The Role of Extracellular Matrix in Human Astrocytoma Migration and Proliferation Studied in a Microliter Scale Assay." Clinical and Experimental Metastasis, 1994; 12(6):405-415.

Fusenig et al. "The Need for a Worldwide Consensus for Cell Line Authentication: Experience Implementing a Mandatory Requirement at the International Journal of Cancer". PLOS Biologiy, Apr. 17, 2017, 15(4) p. e2001438 pp. 1-13.

Giaever et al. "Micromotion of Mammalian Cells Measured Electrically." Proceedings of the National Academy of Sciences, USA, 1991; 88(Sept.):7896-7900.

Henning et al. "Approach to a Multiparametric Sensor-Chip-Based Tumor Chemosensitivity Assay," Anti-Cancer Drugs 2001; 12:21-32.

Hug, Thomas, "Biophysical Methods for Monitoring Cell-Substrate Interactions in Drug Discovery." Assay and Drug Development Technologies, 2003; 1(3):1-10.

Ong et al. "Remote Query Resonant-Circuit Sensors for Monitoring of Bacteria Growth: Application to Food Quality Control." Sensors 2002; 2:219-232.

Simpson et al. "Whole-Cell Biocomputing." Trends in Biotechnology, 2001,19(8):317-323.

Tiruppathi et al. "Electrical Method for Detection of Endothelial Cell Shape Change in Real Time: Assessment of Endothelial Barrier Function." Proceedings of the National Academy of Sciences, USA, 1992, 89:7919-7923.

Wang et al. "Cell Separation by Dielectrophoretic Field-Flow-Fractionation." Analytical Chemistry., 2000, 72:832-839.

Wang et al. "Electronic Manipulation of Cells on Microchip-Based Devices." In Biochip Technology (eds), 2001, pp. 149-177, Harwood Academic Publishers, PA, USA.

Wang et al. "A Theoretical Method of Electrical Field Analysis for Dielectrophoretic Electrode Arrays Using Green's Theorem." Journal of Physics D: Applied Physics, 1996; 29:1649-1660.

Yang et al. "Cell Separation on Microfabricated Electrodes Using Dielectrophoretic/Gravitational field-flow Fractionation." Analytical Chemistry, 1999, 71:911-918.

Yang et al. "A Novel Microfluidic Impedance Assay for Monitoring Endothelin-Induced Cardiomyocyte Hypertrophy." Biosensors and Bioelectronics, 2006, 22:1688-1693.

"Neuro Probe A-Series (AA96, AB96, AC96)" [retrieved from the internet] http://www.neuroprobe.com/protocol/pt_96a.html, 5 pgs.

EP09743420 European Search Report dated Dec. 3, 2012.

PCT/US2009/033801 International Search Report and Written Opinion dated Oct. 30, 2009.

Brustaert et al. "Cardiac Endothelial-Myocardial Signaling: Its Role in Cardiac Growth, Contractile Performance, and Rhythmicity." Physiological Reviews, 2003, 83:59-115.

Jacot et al. "Substrate Stiffness Affects the Functional Maturation of Neonatal Rat Ventricular Myocytes." Biophysics Journal, Oct. 2008, 95:3479-3487.

Mcdevitt et al. "In Vitro Generation of Differentiated Cardiac Myofibers on Micropatterned Laminin Surfaces." Journal of Biomedical Materials Research, 2002, 60:472-479.

Takahashi et al. "Induction of Pluripotent Stem Cells from Mouse Embryonic and Adult Fibroblast Cultures by Defined Factors." Cell, Aug. 25, 2006, 126:663-676.

Takahashi et al. "Induction of Pluripotent Stem Cells from Adult Human Fibroblasts by Defined Factors." Cell, Nov. 30, 2007, 131:861-872.

EP05786773 Extended European Search Report dated Mar. 21, 2013.

EP05852157 Extended European Search Report dated Sep. 13, 2011.

EP058122680 Extended European Search Report dated Sep. 7, 2011.

EP03748948 Extended European Search Report dated Mar. 12, 2007.

EP09743420 European Search Report dated Nov. 26, 2013.

EP10772804.0 Extended European Search Report dated Oct. 27, 2017.

PCT/US2009/033801 International Search Report and Written Opinion dated Jul. 9, 2010.

PCT/US2009/042787 International Search Report and Written Opinion dated Jun. 24, 2009.

PCT/US2011/036877 International Search Report dated Sep. 2, 2011.

PCT/US2013/072439 International Search Report dated Feb. 19, 2014.

PCT/US2005/034561 International Preliminary Report on Patentability dated Mar. 27, 2007.

PCT/US2005/034561 International Search Report dated Sep. 27, 2006.

PCT/US2005/027943 International Preliminary Report on Patentability dated Apr. 11, 2007.

PCT/US2005/027943 International Search Report and Written Opinion dated Mar. 21, 2007.

PCT/US2004/037696 International Search Report dated May 16, 2005.

PCT/US2005/04481 International Search Report dated Sep. 12, 2005.

PCT/US2016/063066 ISR and WO mailed Jan. 30, 2017.

PCT/US2018/044774 ISR and WO mailed Oct. 23, 2018.

Batalov et al. "Differentiation of Cardiomyocytes from Human Pluripotent Stem Cells Using Monolayer Culture." Biomarkers Insights, 2015, 10(s1):71-76.

Brustaert et al. "Cardiac Endothelial-Myocardial Signaling: Its Role in Cardiac Growth, Catractile Performance, and Rhythmicity." Physiological Reviews, 2003, 83:59-115.

Jacot et al. "Substrate Stiffness Affects the Functional Maturatioon of Neonatal Rat Ventricular Myocytes." Biophysics Journal, Oct. 2008, 95:3479-3487.

Lundy et al. "Structural and Functional Maturation of Cardiomyocytes Derived from Human Pluripotent Stem Cells." Stem Cells and Development, 2013, 22(14):1991-2002.

Mcdevitt et al. "In Vitro Generation of Differential Cardiac Myofibers on Micropatterned Laminin Surfaces." Journal of Biomedical Materials Research, 2002, 60:472-479.

Moran et al. "Temporal Trends in Ischemic Heart Disease Mortality in 21 World Regions, 1980 to 2010 The Global Burden of Disease 2010 Study." Circulation, Apr. 8, 2014, 129(14):1483-1492.

Sathaye et al. "Electrical Pacing Counteracts Intrinsic Shortening of Action Potential Duration of Neonatal Rat Ventricular Cells in Culture." Journal of Molecular and Cellular Cardiology, 2006, 41:633-641.

Takahashi et al. "Introduction of Pluripotent Stem Cells from Mouse Embryonic and Adult Fibroblast Cultures by Defined Factors." Cell, Aug. 25, 2006, 126:663-676.

Takahashi et al. "Introduction of Pluripotent Stem Cells from Adult Human Fibroblasts by Defined Factors." Cell, Nov. 30, 2007, 131:861-872.

(56) References Cited

OTHER PUBLICATIONS

Werley et al. "Geometry-dependent functional changes in iPSC-derived cardiomyocytes probed by functional imaging and RNA Sequencing." PLOS One, Mar. 23, 2017, 12(3):e0172671.
Yang et al., "Tri-iodo-L-Thyronine Promotes the Maturation of Human Cardiomyocytes-Derived from Induced Pluripotent Stem Cells." Journal of Molecular Cell Cardiology, Jul. 2014, 72:296-304.
Zimmermann et al. "Tissue Engineering of a Differentiated Cardiac Muscle Construct." Circulation Research, Feb. 8, 2002, 90:223-230.
Maher et al. "Targeting Cytotoxic T Lymphocytes for Cancer Immunotherapy." British Journal of Cancer, 2004, 91:817-821.
EP16867327.5 Supplementary Partial European Search Report dated Jun. 6, 2019.
Carrega et al. "Susceptibility of Human Melanoma Cells to Autologous Natural Killer (NK) Cell Killing: HLA-Related Effector Mechanisms and Role of Unlicensed NK Cells." PLoS One, Dec. 4, 2009, 4(12):e8132.
Peper et al. "An Impedance-Based Cytotoxicity Assay for Real-Time and Label-Free Assessment of T-Cell-Mediated Killing of Adherent Cells," Journal of Immunological Methods, Jan. 29, 2014, 405:192-198.
Oberg et al. "Monitoring Circulating gamma-delta-T Cells in Cancer Patients to Optimize gamma-delta-T Cell-Based Immunotherapy." Frontiers in Immunology, Dec. 17, 2014, 5(643):1-7.
Erskine et al. "Determining Optimal Cytotoxic Activity of Human Her2neu Specific CD8 T Cells by Comparing the CR51 Release Assay to the xCELLigence System," Journal of Visualized Experiments, Aug. 8, 2012, 66(e3683):1-6.
Alici et al. "Autologous Antitumor Activity by NK Cells Expanded from Myeloma Patients Using GMP-Compliant Components," Blood, Mar. 15, 2008, 111(6):3155-3162.
"Label-Free Assay for NK Cell-Mediated Cytolysis," Jan. 1, 2013, pp. 1-8, retrieved from the internet May 23, 2019, URL discloses a method of assessing the effect of e.g. NK cell-mediated cytolysis on target cells using a cell substrate impedance monitoring devices indentical to the one used in the application as filed.
"xCELLigence System Application Table of Contents," Jan. 1, 2014, retrieved from the internet May 23, 2014, URL: https://www.ols-bio.de/media/pdf/Application_Book_09082014_OLS_xs.pdf.
Lamarche et al. Using Impedance-Based Approaches for Measuring Cell-Mediated Cytotoxicity and Antibody-Dependent Cell-Mediated Cytotoxicity (ADCC), Journal of ImmunoTherapy of Cancer, Nov. 4, 2015, 3(Suppl 2): P214.
18760427.7 Extended European Search Report dated Dec. 10, 2020.
Hirt et al. "Functional improvement and maturation of rat and human engineered heart tissue by chronic electrical stimulation," Journal of Molecular and Cellular Cardiology, 2014, 74:151-161.
"xCELLigence RTCA CardioECR System: A Comprehensive Solution for in vitro Cardiac Safety Assessment," Dec. 31, 2014, 1-4 [Retrieved from the Internet: URL: https://www.accela.eu/files/products/51/rtca_cardioecr_brochure.pdf [retrieved on Nov. 30, 2020]].
Abassi, Yama A. "Using Electrical Field Stimulation for Maturation of hiPSC Cardiomyocytes, Assessment of Inotropic Compounds and Cardiac Safety Assessment," Jan. 28, 2019, 1-25 [Retrieved from the Internet: URL: https://www.fda.gov/media/125216/download [retrieved on Nov. 30, 2020]].
Zhang et al. "Functional maturation of human iPSC-derived cardiomyocytes and assessment of inotropic compounds," Journal of Pharmacological and Toxicological Methods, Sep. 13, 2018, 93:170-171.
Aravanis et al. "A Genetically Engineered Cell-Based Biosensor for Functional Classification of Agents." Biosensors & Bioelectronics, 2001,16:571-577.
Banach et al. "Development of Electrical Activity in Cardiac Myocyte Aggregates Derived from Mouse Embryonic Stem Cells." Amerocam Journal of Physiology-Heart Circulatoy Physiology, 2003, 284: H2114-H2123.
Baumann et al., "Microelectronic Sensor System for Microphysical Application on Living Cells", Sensors and Actuators, 1999:77-89.

Becker et al. "Separation of Human Breast Cancer Cells from Blood by Differential Dielectric Affinity." Cell Biology, 1995, 92:960-964.
Berdondini et al. "High-Density Electrode Array for Imaging in Vitro Electrophysiological Activity." Biosensors and Bioelectronics, 2005, 21:167-174.
Berens et al. "The Role of Extracelluar Matrix in Human Astrocytoma Migration and Proliferation Studied in a Microliter Scale Assay." Clinical and Experimental Metastasis, 1994; 12(6):405-415.
Bergveld, P. "A Critical Evaluation of Direct Electrical Protein Detection Methods." Biosensors & Bioelectronics. 6:55-72(1991).
Bieberich et al. "Neuronal Differentiation and Synapse Formation of PC12 and Embryonic Stem Cells on Interdigitated Microelectrode Arrays," Biosensors and Bioelectronics 2004; 19:923-931.
Blagbrough et al. "Polyamines and Novel Polyamine Conjugates Interact with DNA in Ways That Can Be Exploited in Non-Viral Gene Therapy." Biochemical Society Transactions, 2003, 31, Part 2, pp. 397-406.
Bonetta, Laura. "The Inside Scoop-Evaluating Gene Delivery Methods." Nature Methods, Nov. 2005, 2(11):875-883.
Burnett et al. "Fluorescent Imaginng of Electrically Stimulated Cells." Journal of Biomolecular Screening 2003; 8(6):660-667.
Burns et al. "Neutrophil Transendothelial Migration Is Independent of Tight Junctions and Occurs Preferentially at Tricellular Corners." Journal of Immunology, 1997, 2893-2903.
Cady et al. "Electrical Impedance Measurements: Rapid Method for Detecting and Monitoring Microorganisms," Journal of Clinical Mirobiology, 1978; 7(3):265-272.
Cartellieri et al. "Chimeric Antigen Receptor—Engineered T Cells for Immunotherapy of Cancer." Journal of Biomedicine and Biotechnology, 2010, 1-13.
Chang et al. "Impedimetric Monitoring of Cell Attachment on Interdigitated Microelectrodes." Sensors and Actuators, 2005, B 105:159-163.
Ciambrone et al. "Cellular Dielectric Spectroscopy: A Powerful New Approach to Label-Free Cellular Analysis." Journal of Biomolecular Screening, 2004, 9(6):467-480.
Connolly et al. "An Extracellular Microelectrode Array for Monitoring Electrogenic Cells in Culture," Biosensors and Biolectronics, 1190, 5:223-234.
Duan et al. "Separation-Free Sandwich Enzyme Immunoassays Using Microporous Gold Electrodes and Self-Assembled Monolayer/Immobilized Capture Antibodies." Analytical Chemistry, 1994, 66:1369-1377.
Ehret et al. "Monitoring of Cellular Behaviour by Impedance Measurements on Interdigitated Electrode Structures." Biosensors and Bioelectronics 1997; 12(1):29-41.
Ehret et al. "On-Line Control of Cellular Adhesion with Impedance Measurements Using Interdigitated Electrode Structures", Medical & Biological Engineering & Computing, 1998; 36:365-370.
Falk et al. "A 48-well Micro Chemotaxis Assembly for Rapid and Accurate Measurement of Leukocyte Migration." Journal of Immunological Methods., 1980, 33:239-247.
Fuhr et al. "Positioning and Manipulation of Cells and Microparticles Using Miniaturized Electric Field Traps and Travelling Waves." Sensors and Materials 7(2):131-146 (1995).
Fusenig et al. "The Need for a Worldwide Consensus for Cell Line Authentication: Experience Implementing a Mandatory Requirement at the Internation Journal of Cancer". PLOS Biologiy, Apr. 17, 2017, 15(4) p. e2001438 pp. 1-13.
Giaever et al, "Monitoring Fibroblast Behavior in Tissue Culture with an Applied Electric Field." Proceedings of the National Academy of Sciences. USA; 1984; 81(June):3761-3764.
Giaever et al. "Micromotion of Mammalian Cells Measured Electrically." Proceedings of the National Academy of Sciences, USA, 1991; 8(Sept.):7896-7900.
Gutmann et al. "Evidence for Different ABC-Transporters in Caco-2 Cells Modulating Drug Uptake." Pharmaceutical Research, 1999, 16(3):402-407.
Hadjout et al. "Automated Real-Time Measurement of Chemotactic Cell Motility." BioTechniques, 2001, 31:1130-1138.
Hapala, Ivan. "Breaking the Barrier: Methods for Reversible Permeabilization of Cellular Membranes." Critical Reviews in Biotechnology, 1997, 17(2):105-122.

(56) References Cited

OTHER PUBLICATIONS

Henning et al. "Approach to a Mutliparametric Sensor-Chip-Based Tumor Chemosensitivity Assay," Anti-Cancer Drugs 2001; 12:21-32.
Hescheler et al. "Determination of Electrical Properties of ES Cell-derived Cardiomyocytes Using MEAs." Journal of Electrocardiology, 2004, vol. 37, Suppl.
Hidalgo et al. "Characterization of the Human Colon Carcinoma Cell Line (Caco-2) as a Model System for Intestinal Epithelial Permeability," Gastroenterology, 1989; 96:736-749.
Horvath et al. "Monitoring of Living Cell Attachment and Spreading Using Reverse Symmetry Waveguide Sensing." Applied Physics Letters, 2005, 86:071101.
Huang et al. "Dielectrophoretic Cell Separation and Gene Expression Profiling on Microelectronic Chip Arrays." Analytical Chemistry, 2002, 74:3362-3371.
Hug, Thomas, "Biophysical Methods for Monitoring Cell-Substrate Interactions in Drug Discovery." Assay and Drug Development Technologies, 2003; 1(3):479-488.
Keese et al. "Real-time Impedance Assay to Follow the Invasive Activities of Metastatic Cells in Culture." BioTechniques, 2002, 33:842-850.
Klauke et al. "Extracellular Recordings of Field Potentials from Single Cardiomyocytes." Biophysical Journal, Oct. 2006, 91:2543-2551.
Kleinman et al. "Basement Membrane Complexes with Biological Activity." Biochemistry 1986; 25(2):312-318.
Kloss et al. "Microcavity Array (MCA)-Based Biosensor Chip for Functional Drug Screening of 3D Tissue Models." Biosensors and Bioelectronics, 2008, 23:1473-1480.
Kowolenko et al. "Measurement of Macrophage Adherence and Spreading with Weak Electric Fields." Journal of Immunological Methods, 1990; 127:71-77.
Larsen et al. "Somatic Cell Counting with Silicon Apertures." Micro Total Analysis Systems, 2000, 103-106.
Lin et al. "Electroporation Microchips for In Vitro Gene Transfection." Journal of Micromechanics and Microengineering, 2001, 11:542-547.
Lin et al. "Simulation and Experimental Demonstration of the Electric Field Assisted Electroporation Microchip for In Vitro Gene Delivery Enhancement." Miniaturisation for Chemistry, Biology & Bioengineerin., 2004, 4:104-108.
Lo et al. American Physical Society March Meeting 2010, Portland Oregon, vol. 55, No. 2, Poter Session Abstract, BAPS, Mar. 2010 C1 268.
Lo et al. "Monitoring Motion of Confluent Cells in Tissue Culture." Experimental Cell Research 1983; 204:102-109.
Lo et al. "Impedance Analysis of MDCK Cells Measured by Electric Cell-Substrate Impedance Sensing." Biophysical Journal, 1995, 69:2800-2807.
Lo et al. "pH Changes in pulsed CO2 incubators cause periodic changes in cell morphology." Experimental Cell Research, 1994, 213:391-397.
Loffert et al. "Multiplex PCR with QIAGEN: Taq DNA Plymerase and PCR Buffer." QIAGENews, 1994, 4:15-18.
Luan et al. "Clustering of Time-Course Gene Expression Data Using a Mixed-Effects Model with B-Splines." Bioinformatics, 2003, 19(4):474-482.
Luong et al. "Monitoring Motility, Spreading and Mortality of Adherent Insect Cells Using an Impedance Sensor.", Analytical Chemistry, 2001, 73(8):1844-1848.
Mitra et al. "Electric Measurements Can Be Used to Monitor the Attachment and Spreading of Cells in Tissue Culture." Biotechniques, 1991, 11(4):504-510.
Miyata et al. "New Wound-Healing Model Using Cultured Corneal Endothelial Cells." Japan Journal of Opthalmology, 1990, 34:257-266.
Mohr et al. "Performance of a Thin Film Microelectrode Array for Monitoring Electrogenic Cells in Vitro." Sensors and Actuators, B34:265-269 (1996).
Neher, Erwin, "Molecular Biology Meets Microelectronics." Nature Biotechnology, 2001; 19:114.
Nerurkar et al. "The Use of Surfactants to Enhance the Permeability of Peptides Through Caco-2 Cells by Inhibition of an Apically Polarized Efflux System." Pharmaceutical Research, 1996,13(4):528-534.
Nicolazzi et al. "Cationic Lipids for Transfection." Current Medicinal Chemistry, 2003, 10:1263-1277.
Oka et al. "A New Planar Multielectrode Array for Extracellular Recording: Application to Hippocampal Acute Slice." Journal of Neuroscience Methods, 1999, 93:61-67, Elsevier Science, B.V.
Ong et al. "Remote Query Resonant-Circuit Sensors for Monitoring of Bacterial Growth: Application to Food Quality Control." Sensors 2002; 2:219-232.
Pancrazio et al. "Portable Cell-Based Biosensor System for Toxin Detection." Sensors and Actuators 1998; 53:179-185.
Patolsky et al. "Detection of Single-Base DNA Mutations by Enzyme-Amplified Electronic Transduction." Nature Biotechnology, 2001, 19:253-257.
Pethig et al. "Positive and Negative Dielectrophoretic Collection of Colloidal Particles Using Interdigitated Castellated Microelectrodes." Applied Physics, 1992, 24:881-888.
Qiu et al. "Real-Time Monitoring Primary Cardiomyocyte Adhesion Based on Electrochemical Impedance Spectroscopy and Electrical Cell-Substrate Impedance Sensing" Analytical Chemistry, 2008, 80:990-996.
Rabow et al. "Mining the National Cancer Institute's Tumor-Screening Database: Identification of Compounds with Similar Cellular Activities." Journal of Medicinal Chemistry, 2002, 45:818-840.
Richards et al. "A Modified Microchamber Method for Chemotaxis and Chemokinesis." Immunological Communications, 1984, 13 (1):49-62.
Rishpon et al. "An Amperometric Enzyme-channeling Immunosensor." Biosensors & Bioelectronics, 1997, 12 (3):195-204.
Simpson et al. "Whole-Cell Biocomputing." Trends in Biotechnology, 2001, 19(9):317-323.
Slaughter et al. "Artificial Neural Network for Temporal Impedance Recognition of Neurotoxins." 2006 International Joint Conference on Neural Networks 2006; Jul. 16-21: 2001-2008.
Sohn et al. "Capacitance Cytometry: Measuring Biological Cells One by One." Proceedings of the National Academy of Sciences, 2000, 97(20):10687-10690.
Steinem et al. "Impedance and Shear Wave Resonance Analysis of Ligand-Receptor Interactions at Functionalized Surfaces and of Cell Monolayers." Biosensors & Bioelectronics, 1997, 12(8):787-808.
Stenger et al. "Detection of Physiologically Active Compounds Using Cell-Based Biosensors." Trends in Biotechnology, 2001; 19(8):304-309.
Svetlicic et al. "Charge Displacement by Adhesion and Spreading of a Cell." Bioelectrochemistry, 2000, 53:79-86.
Tiruppathi et al. "Electrical Method for Detection of Endothelial Cell Shape Change in Time: Assessment of Endothelial Barrier Function." Proceedings of the National Academy of Sciences, USA, 1992, 89:7919-7923.
Wang et al. "Selective Dielectrophoretic Confinement of Bioparticles in Potential Energy Wells." Applied Physics, 1993, 26:1278-1285.
Wang et al. "Cell Separation by Dielectrophoretic Field-Flow-Fractionation." Analyitcal Chemistry., 2000, 72:832-839.
Wang et al. "Dielectrophoretic Manipulation of Cells with Spiral Electrodes." Biophysical Journal, 1997, 72:1887-1899.
Wang et al. "Separation of Polystyrene Microbeads Using Dielectrophoretic/Gravitational Field-Flow-Fractionation." Biophysical Journal, 1998, 74:2689-2701.
Wang et al. "Electronic Manipulation of Cells on Microchip-Based Devices." In Biochip Technology (eds), 2001, pp. 135-159, Harwood Academic Publishers, PA, USA.
Wang et al. "A Theoretical Method of Electrical Field Analysis for Dielectrophoretic Electrode Arrays Using Green's Theorem." Journal of Phyics D: Applied Physics, 1996; 29:1649-1660.
Warburg Ueber die Polarisationscapacitat des Platins. Annals of Physics, 6:125-135 (1901).

(56) References Cited

OTHER PUBLICATIONS

Wegener et al. "Electric Cell-Substrate Impedance Sensing (ECIS) as Noninvasive Means to Monitor the Kinetics of Cell Spreading to Artificial Surfaces." Experimental Cell Research 2000; 259:158-166.

Wegener et al., Use of Electrochemical Impedance Measurements to Monitor Beta-Adrenergic Stimulation of Bovine Aortic Endothelial Cells. European Journal of Physiology, 437:925-934 (1999).

Wolf et al. "Monitoring of Cellular Signalling and Metabolism with Modular Sensor-Technique: The PhysioControl-Microsystem (PCM)." Biosensors and Bioelectronics 1998; 13:501-509.

Xiao et al. "Assessment of Cytotoxicity Using Electric Cell-Substrate Impedance Sensing: Concentration and Time Response Function Approach." Analytical Chemistry, 2002, 74:5748-5753.

Xiao et al. "An In-Depth Analysis of Electric Cell-Substrate Impedance Sensing to Study the Attachment and Spreading of Mammalian Cells." Analytical Chemistry, 2002; 74(6):1333-1339.

Xiao et al. "On-Line Monitoring of Cell Growth and Cytotoxicity Using Electric Cell-Substrate Impedance Sensing (ECIS)." Biotechnology Progress, 2003; 19:1000-1005.

Xing et al. "Dynamic Monitoring of Cytotoxicity on Microelectronic Sensors" Chemical Research in Toxicology., 2005, 18(2):154-161.

Yamauchi et al. "Spatially and Temporally Controlled Gene Transfer by Electroporation into Adherent Cells on Plasmid DNA-Loaded Electrodes." Nucleic Acids Research, 2004, 32(22):1-8.

Yang et al. "Celli Separation on Microfabricated Electrodes Using Dielectrophoretic/Gravitational field-flow Fractionation." Analytical Chemistry, 1999, 71:911-918.

Yang et al. "A Novel Microfluidic Impedance Assay for Monitoring Endothelin-Induced Cardiomyocyte Hypertrophy." Biosensors and Bioelectronics, 2007, 22:1688-1693.

Yu et al. "Real-Time Monitoring of Morphological Changes in Living Cells by Electronic Cell Sensor Arrays: An Approach To Study G Protein-Coupled Receptors." Analytical Chemistry, 2006, 78:35-43.

"Automated Cell Monitoring Instrument." Applied BioPhysics, 2002, [retrieved from the internet] http://www.biophysics.com/pages/front.html, 1 page.

"Cell Migration Studies with TECAN Systems." TECAN., Sep. 1999, [retrieved from the internet] http://www.tecan.com/migration_introl.pdf, 10 pgs.

"Detect Cell Migration and Invasion in a Homogeneous Fluorescent Assay System." BD Biosciences, http://www.bdbiosciences.com/discovery_labware/Products/inserts/BD_Falcon_HTS_fluoroblok_inserts/individual_fluoroblok_inserts/index.html, 2004.

HP 4284A Precision LCR Meter Operation Manual, Aug. 1998, Hewlett Packard, 6th Edition, p. 1-460.

"Molecular Viewer" New Products page. Science 298:2409 (2002).

"Neuro Probe AA96, AB96, AC96 Chemotaxis Chambers." Neuro Probe, [retrieved from the internet] http://www.neuroprobe.com/protocol/pt_96a.html, 5 pgs.

CA2556219 Office Action dated Aug. 9, 2010.

CA2575573 Office Action dated Apr. 4, 2012.

EP05722991 Extended European Search Report dated Apr. 3, 2009.

EP11193882 Extended European Search Report dated Apr. 5, 2012.

EP13171137 Extended European Search Report dated Aug. 16, 2013.

Burnett et al. "Fluorescence Imaging of Electrically Stimulated Cells." Journal of Biomolecular Screening 2003; 8(6):660-667.

Office Action dated Dec. 2, 2022 for CN 100089.

Acea Biosciences, xCELLigence RTCA CardioECR System, https://www.accela.eu/files/products/51/Yrtca_cardioecr_brochure.pdf, Dec. 31, 2014.

Office Action dated Dec. 2, 2022 for CN 201880029024.6.

* cited by examiner

| | Iso (100 nM) | Bay K8644 (67 nM) | Pimobendan (10 µM) | Milrinone (30 µM) | OM (600 nM) | Digoxin (100 nM) | Bradipine (10 nM) |
|---|---|---|---|---|---|---|---|
| MOA | β adrenergic receptor agonist | L-type Ca 2+ ion channel activator | Ca 2+ sensitizer | phosphodiesterase-3 inhibitor | Myosin activator | Na-K ATP exchanger inhibitor | L-type Ca 2+ ion channel inhibitor |
| Inotropic effect | + | + | + | + | + | + | − |
| Screenshot — Pre-drug — Post-drug | | | | | | | |
| % change (BAmp) | 52 ± 14% | 32 ± 5% | 31 ± 6% | 30 ± 12% | 58 ± 15% | 175 ± 35% | −47 ± 7% |
| % change (BR) | 73 ± 7% | −23 ± 2% | 3 ± 2% | 14 ± 3% | −3 ± 4% | −49 ± 30% | 20 ± 2% |

FIG. 8

METHODS AND SYSTEMS FOR FUNCTIONAL MATURATION OF IPSC AND ESC DERIVED CARDIOMYOCYTES

CROSS REFERENCE TO RELATED APPLICATIONS

This application is a US national phase application under 35 USC § 371 of international patent application no. PCT/US2018/020817, filed Mar. 3, 2018, which itself claims benefit of priority to U.S. provisional patent application No. 62/466,992, filed Mar. 3, 2017 and U.S. provisional patent application No. 62/490,505, filed Apr. 26, 2017; the entire content of each is herein incorporated by reference in its entirety.

TECHNICAL FIELD

The invention is directed to methods for electrically inducing maturation of iPSC and ESC-derived cardiomyocytes into cells having an adult-like phenotype and for electrically monitoring the maturation process.

BACKGROUND OF THE INVENTION

Induced pluripotent stem cells (iPSC) are a type of pluripotent stem cell that can be generated directly from adult cells. This technology was pioneered over a decade ago by the introduction of four specific genes encoding transcription factors Oct3/4, Sox2, c-Myc and Klf4 into mouse adult fibroblasts under embyronic stem (ES) cell culture conditions. Takahashi et al. (2006). Takahashi et al. later demonstrated their factors also worked on humans. Takahashi et al. (2007).

The use of iPSCs holds enormous promise for regenerative medicine applications as well as drug discovery and development. In particular, iPSCs can be differentiated into many different types of cells such as neurons, cardiomyocytes and hepatocytes for potential therapies. These cells can also be used for understanding underlying disease mechanisms and screening for therapeutics which may serve to alleviate disease conditions. One of the first cell types derived from iPSC technology was cardiomyocytes. These iPSC-derived cardiomyocytes appear to express the proper ion channel repertoire, as well as structural and other proteins found in normal cardiomyocytes. However, it is challenging to fully differentiate iPSCs into cardiomyocytes having an adult phenotype. Rather, development often stalls during the immature phase, where, compared to the mature or adult phenotype, the immature cardiomyocytes tend to have a rounded morphology, disorganized sarcomere, lack of T-tubule, differ in gene expression profile, and differ in action potential profile. The potential for immature cardiomyocytes as a therapeutic approach is limited. Yang et al. (2014).

A variety of different approaches have been employed to improve maturation status of iPSC-derived cardiomyocytes, including long-term cardiomyocyte culture (Lundy et al, 2013), cultivation of cells on a substrate which has stiffness close to that of native myocardium (Jacot et al., 2008), seeding cells to a patterned substrate providing topographical cues (McDevitt et al., 2002), applying mechanical loading to cells (Zimmermann et al., 2002), and directed electrical stimulation (Sathaye et al., 2006). All these methods can result in cardiomyocytes that structurally and functionally resemble an adult-like phenotype. However each system has its weaknesses, such as difficulty to achieve high throughput screening, and the high level of technical knowledge required.

Accordingly, there remains a need for improved systems and methods for further maturation of cardiomyocyte precursor cells, including iPSC derived and embryonic stem cell (ESC) derived cardiomyocytes into those having mature or an adult-like phenotype.

BRIEF SUMMARY OF THE INVENTION

The invention address the above deficiencies and provides related benefits. In particular, the invention provides methods and systems that electrically induce further maturation of iPSC or ESC-derived cardiomyocytes and electrically monitor their maturation into a more adult-like phenotype. This is accomplished, at least in part, by expanding the electrical pacing and monitoring features of the xCELLigence CardioECR system, developed by ACEA Biosciences, Inc. (San Diego, Calif.) to systematically pace iPSCs and other immature cardiomyocytes using pulse profiles specifically developed to induce maturation while also monitoring the beating profile of cells in culture to monitor the maturation process.

More specifically, in one aspect of the invention a method of maturing functionally immature cardiomyocytes is provided, the method including: providing a system configured to culture, electrically pace, and monitor beating of beating cells; culturing immature cardiomyocytes in the system; monitoring the immature cardiomyocytes to characterize cardiomyocyte beating as synchronized or not synchronized; and if synchronized, electrically pacing the immature cardiomyocytes according to a pulse profile until the immature cardiomyocytes mature into functionally adult cardiomyocytes.

In some embodiments, the system includes an impedance monitoring electrode array positioned on a substrate and operably connected to an impedance analyzer to monitor cell-substrate impedance of a cell population cultured in the system. In other embodiments, the system includes an extracellular recording electrode array operably connected to an extracellular recording amplifier to conduct extracellular recording of a cell population cultured in the system. In still other embodiments, system is configured to monitor cell-substrate impedance and conduct extracellular recording of a cell population cultured in the system by providing both, such as an impedance monitoring electrode array on a substrate, an extracellular recording electrode array on the substrate, an impedance analyzer, and an extracellular recording amplifier. In some embodiments an electrode is shared between the cell-substrate impedance monitoring electrode array and the extracellular recording electrode array but in other embodiments, each has its own distinct pair of electrodes.

Among the improvements provided, is the ability to differentiate cardiomyocytes starting from different levels or degrees of immaturity without regard to beating rate in culture. That is, the methods herein are useful for inducing maturation in any cardiomyocyte cell population deemed immature, characterized by a negative force-frequency relationship. To this end, cardiomyocytes characterized as immature, also referred to herein having an embryonic phenotype, can be used as long as the cells undergo excitation contraction coupling. As such, the immature cardiomyocytes can be derived from induced pluripotent stem cells (iPSCs) or embryonic stem cells (ESCs).

Further, the immature cardiomyocytes can be electrically monitored to characterize their stage as immature or adult, and to assess their suitability to undergo further differentiation. Among the approaches useful in monitoring maturation of cardiomyocytes include monitoring cell-substrate impedance of the cardiomyocytes. In other embodiments, immature cardiomyocytes are electrically monitored by extracellular recording of the cardiomyocytes. In a hybrid approach, immature cardiomyocytes are electrically monitored by cell-substrate impedance monitoring of the cardiomyocytes and extracellular recording of the cardiomyocytes. Electrical measurement of cardiomyocyte beating permits a force-frequency relationship to be determined, where a positive force-frequency relationship is indicative of a mature cardiomyocyte population and a negative force frequency relationship is indicative of an immature cardiomyocyte population.

In addition, electric monitoring of the immature cardiomyocytes can be used to determine whether cardiomyocyte beating is synchronized, such as by determining a beating rate of the immature cardiomyocytes and comparing the beating rate over time. If cardiomyocyte beating is not synchronized, the immature cardiomyocytes may require additional culturing. Electric pacing of immature cardiomyocytes can also be used to induce synchronized beating of immature cardiomyocytes. Inducing synchronized beating electrically can be accomplished by applying electric pulses at a constant frequency. In particular, the electric pulses are typically provided at the same rate or at about the same rate as the beating rate of the immature cells. Generally, a pulsing frequency of about 0.5 Hz to 1 Hz can help synchronize beating.

Once beating is synchronized, the immature cardiomyocytes are electrically paced according to a pulse profile to induce further maturation into a functionally mature or adult phenotype. These pulse profiles were developed to induce maturation in iPSC derived, ESC derived and functionally immature cardiomyocytes. An exemplary pulse profile has a rectangular pulse shape. An exemplary pulse intensity of 0.7 V to 1 V, with intensities or voltages up to multiple volts (e.g. 2 V or 3 V) are acceptable. The pulse intensity should be sufficiently high to result in pacing of the immature cardiomyocytes (i.e. each applied pulse could lead to a beating cycle of the cardiomyocytes in the device).

An exemplary pulse profile has a pulse duration or width from 0.1 milliseconds to 0.2 milliseconds with duration up to 10 milliseconds being acceptable. With appropriately applied pulse intensity, pulse duration should be sufficiently long to result in pacing of the cardiomyocytes (i.e. each applied pulse could lead to a beating cycle of the cardiomyocytes in the device). Generally the pulse duration should be applied as short as possible, as long as it leads to the effective pacing of the cardiomyocytes (i.e. each applied pulse could lead to a beating cycle of the cardiomyocytes in the well).

Differentiating immature cardiomyocytes using the system is primarily accomplished by way of applying a pulse profile with a varying pulse frequency to pace immature cardiomyocytes over time. The skilled artisan will appreciate that the pulse profile can vary depending on the beating rate of the immature cardiomyocytes and can also vary depending on the method used to differentiate immature cardiomyocytes into mature cardiomyocytes. As an example, a pulse profile will typically start at a frequency that matches or nearly matches the beating rate of the immature cardiomyocytes, which can vary. Most often, the pulse profile will start at a slower pulse frequency and increase in frequency over time. This initial lower pulse frequency should be appropriate so that the cardiomyocyte can follow the pacing pulses (i.e. each pacing pulse could result in one beating cycle of the cardiomyocytes in the device). As an example, a pulse profile was developed to have a pulse frequency that varies between 0.5 Hz and 2 Hz over time. As another example, the pulse profile includes a pulse frequency that varies between 1 Hz and 2 Hz over time. As another example, the pulse profile includes a pulse frequency that increases from 0.75 Hz to 2 Hz over time. As another example, the cardiomyocytes of certain genotype or phenotype, such as a diseased genotype/phenotype, may require an initial lower pulse frequency such as 0.5 Hz, or 0.3 Hz or even lower so that the cardiomyocytes can be effectively paced. On the other hand, the pulse frequency can be increased over time from an initial low pulse rate to a higher pulse frequency such as 3 Hz, or even higher, depending on the requirement of the assays that would use such cardiomyocytes that are being paced. The skilled artisan will appreciate that the time period between increasing the pulse frequency can also vary but in some embodiments, the time period for increasing the pulse frequency occurs over 2-6 days. In other embodiments, time period for increasing the pulse frequency occurs over 1 to 5 weeks. As a nonlimiting example, further differentiation of immature cardiomyocytes can occur when pulsing at 0.75 Hz for 1 week, 1.5 Hz for another week, and 2 Hz for still another week. Preferably the increasing pulse frequency doubles in frequency over time. Cardiomyocyte maturation can be followed by periodically testing the force-frequency relationship of the beating culture to determine whether the force-frequency relationship increases, which is indicative of maturity, or decreases, which is indicative of immaturity. In particular, testing can include progressively increasing the pacing rate of the cardiomyocytes and simultaneously recording the beating amplitude, which is a surrogate for force. If there is a negative beating amplitude/electrical pacing rate relationship then the cardiomyocyte is deemed immature; whereas if there is a positive amplitude/electrical pacing rate relationship, the cardiomyocyte is deemed "mature".

Functionally mature or adult cardiomyocytes have a positive force-frequency relationship; whereas immature cardiomyocytes have a negative force-frequency relationship. Thus, by electrically monitoring a parameter that corresponds to beating force, such as a beating amplitude measurement, the force-frequency relationship can be assessed to monitor the maturation process. As such, the methods include electrically pacing immature cardiomyocytes until the cardiomyocytes are characterized as having a positive force-frequency relationship, which is indicative of an adult phenotype.

In a related aspect of the invention, a method of characterizing an effect of a compound on cardiomyocyte beating is provided. The method includes providing a system configured to culture, electrically pace, and monitor beating of contracting cells; culturing immature cardiomyocytes in the system; electrically pacing the immature cardiomyocytes according to a pulse profile until the cardiomyocytes are functionally mature; adding a compound suspected of having an effect on cardiomyocyte beating force or cardiomyocyte beating rate to the functionally mature cardiomyocytes; electrically monitoring the cultured cardiomyocytes before and after compound addition; determining before and after compound addition, at least one parameter that characterizes a beating amplitude or a beating rate; comparing the determined at least one parameter before and after compound addition thereby identify a difference in response to the compound addition; and characterizing the compound as: a positive inotropic compound if the beating amplitude increases after compound addition or a negative inotropic compound if the beating amplitude decrease after compound addition, and/or a positive chronotropic compound if the beating rate increases after the compound addition or a negative chronotropic compound if the beating rate decreases after the compound addition.

In view of the technical improvements herein, the method may be used with immature cardiomyocytes derived from induced pluripotent stem cells (iPSCs) or embryonic stem cells (ESCs). The immature cardiomyocytes are preferably cultured until beating is synchronized. Synchronized beating is preferably determined by way of electrical measurement but could be determined optically. As non-limiting examples, the electrical measurement can be cell-substrate impedance monitoring, extracellular recording, or both cell-substrate impedance monitoring and extracellular recording. If the beating is not synchronized, the cardiomyocytes can be electrically paced until cardiomyocyte beating is synchronized. Such electric pulses may be at a constant frequency.

Pacing cardiomyocytes to achieve a more mature or adult phenotype for testing the effect of one or more compounds includes applying a pulse profile able to induce further maturation. Such a pulse profile can be characterized as having a rectangular pulse shape, an intensity of about 0.1 V to 0.2 V (up to 2 or 3 volts), and a pulse duration from 0.1 milliseconds to 0.2 milliseconds (up to 10 milliseconds).

Further differentiation of an immature cardiomyocyte population into one that can be characterized as having an adult phenotype can accomplished by way of applying a pulse profile with a varying pulse frequency. In particular, a pulse profile starting at a slower pulse frequency and increasing in frequency over time. As a nonlimiting example, a pulse profile for cardiomyocyte differentiation was developed to have a pulse frequency that varies between 0.3 Hz and 3 Hz over time. More preferably, the pulse profile includes a pulse frequency that varies between 0.5 Hz and 2 Hz over time. More preferably, the pulse profile includes a pulse frequency that varies between 1 Hz and 2 Hz over time. In a particularly preferred approach, the pulse profile includes a pulse frequency that increases from 0.75 Hz to 2 Hz over time. The time period between increasing the pulse frequency can vary but in some embodiments, the time period for increasing the pulse frequency occurs over 2-6 days. In other embodiments, time period for increasing the pulse frequency occurs over 1 to 5 weeks. As further guidance, immature cardiomyocytes may be pulsed at 0.75 Hz for 1 week, 1.5 Hz for another week, and 2 Hz for still another week to induce and maintain a mature phenotype. Preferably the increasing pulse frequency doubles in frequency over time.

Combining a synchronized beating culture with high resolution electric monitoring of the culture also permits identifying changes in beating amplitude and beating rate in response to the administration of compounds. To this end, the method permits characterizing the effect of potential drugs on cardiomyocytes and can therefore be used to develop new therapeutics or new therapeutic uses of known compounds. As a nonlimiting example, the method can electrically detect changes in the cardiomyocyte cell population in response to the administration of a vasodilator. These changes can be assessed by electrically monitoring the cultured cardiomyocytes before and after compound addition by way of monitoring cell-substrate impedance of the cardiomyocytes, performing extracellular recording of the immature cardiomyocytes, or both monitoring cell-substrate impedance of the cardiomyocytes and performing extracellular recording of the immature cardiomyocytes.

In yet another related aspect, a method of characterizing an effect of a compound on cardiomyocyte maturation is provided, the method including: providing a system configured to culture, electrically pace, and monitor beating of contracting cells; culturing immature cardiomyocytes in the system; electrically pacing the immature cardiomyocytes according to a pulse profile that functionally matures the cardiomyocytes; adding a compound suspected of having an effect on cardiomyocyte maturation; electrically monitoring the cultured cardiomyocytes before and after compound addition; determining before and after the compound addition, at least one parameter that characterizes beating force-frequency relationship of the monitored cardiomyocytes; comparing the determined at least one parameter before and after the compound addition thereby identify a difference in response to the compound addition.

In still another related aspect, a method of characterizing an effect of a compound on cardiomyocyte beating is provided, which includes: providing a system configured to culture, electrically pace, and monitor beating of contracting cells; culturing two populations of immature cardiomyocytes in the system; adding a compound suspected of having an effect on cardiomyocyte maturation to one of the populations of immature cardiomyocytes; electrically pacing the two populations of immature cardiomyocytes according to a pulse profile that functionally matures immature cardiomyocytes until at least one of the two populations of cardiomyocytes is functionally mature; and characterizing the compound as further driving maturation if the population with compound addition functionally matures before the other cardiomyocyte population.

In still another related aspect, a system for the functional maturation of immature cardiomyocytes is provided. The system includes: an electronic pulse generator configured to deliver electronic pulses according to a pulse profile that induces maturation of immature cardiomyocytes; a device station configured to engage a cell culture device and deliver the electronic pulses from the pulse generator to the engaged cell culture device; a cell culture device having a substrate configured to culture cells, each substrate having an electrode array addressable by the device station when engaged; and a module for electrically monitoring cultured cells.

In view of methods for cardiomyocyte differentiation described herein, the pulse generator can deliver electronic pulses with a pulse shape as a rectangular shape. In some embodiments, the pulse generator delivers an intensity of 0.1 V to 0.2 V to 2 volts. In other embodiments the pulse generator delivers an intensity of up to 3 volts. In some embodiments the pulse generator delivers a pulse duration from 0.1 millisecond to 0.2 milliseconds to 10 milliseconds.

In some embodiments, the device station has an interface with a plurality of electrical contacts and a switch capable of independently delivering the electronic pulses to each of the electrical contacts. In some embodiments, device station is configured to accept a multi-well plate, optionally a plurality of multi-well plates. In such embodiments, the electronic pulse generator and the device station can be configured to deliver a pulse simultaneously to more than one well of the multi-well plate. Further, the electronic pulse generator and the device station can be configured to deliver a pulse simultaneously to all wells of the multi-well plate. Still further, in some embodiments, the electronic pulse generator and the device station are configured to deliver a pulse simultaneously to more than one multi-well plate. In some embodiments, the electronic pulse generator and the device station are configured to deliver different pulse profiles to different wells of the multi-well plate. In other embodiments, the device station is configured to engage one or more cell culture flasks.

In some embodiments, the cell culture device is a flask. In other embodiments, the culture device is a multi-well plate, optionally selected from the group consisting of a 6 well plate, a 48 well plate, and a 96 well plate.

In some embodiments, the system includes immature cardiomyocytes in culture on the substrate of the cell culture device. Exemplary cardiomyocytes include immature cardiomyocytes derived from induced pluripotent stem cells (iPSCs) or embryonic stem cells (ESCs).

The module for electrically monitoring cultured cells can include an impedance analyzer operably connected for monitoring cell-substrate impedance of a cell population cultured in the cell culture device. In other embodiments, the module for electrically monitoring cultured cells includes an extracellular recording amplifier operably connected for extracellular recording of a cell population cultured in the cell culture device. In still further embodiments the module for electrically monitoring cultured cells includes an impedance analyzer operably connected for monitoring cell-substrate impedance of a cell population cultured in the cell culture device and an extracellular recording amplifier operably connected for extracellular recording of a cell population cultured in the cell culture device.

BRIEF DESCRIPTION OF THE DRAWINGS

FIG. 8 is a table showing a summary of quantitative inotropic compound effects on contractile activity of functional matured iCell cardiomyocytes after pacing at representative concentrations. Data are presented as mean±SD. (N=5).

DETAILED DESCRIPTION OF PREFERRED EMBODIMENTS

The invention is directed towards systems and methods that culture, electrically pace, and monitor the maturation of immature cardiomyocytes into cells having an adult-like phenotype. In particular, the systems and methods are able to induce and electrically monitor functional maturation of iPSC derived cardiomyocytes and embryonic stem cell (ESC) derived cardiomyocytes. Further, the systems and methods provide a new approach for testing inotropic compounds, chronotropic compounds and testing compounds that affect the cardiomyocyte maturation process.

A. Systems for Electrically Pacing and Electrical Measurement of Cells

A central advantage to systems described herein is that they can electrically induce further maturation of embryonic stem cell derived cardiomyocytes and iPSC derived cardiomyocytes. Preferred systems pair an electrode-based monitoring system together with an electrostimulating system to provide immediate feedback as to the functional phenotype of a maturing cell population in response to electrostimulation. In the preferred approaches the system includes electrostimulation to induce differentiation while providing high resolution parallel impedance-based monitoring and/or parallel extracellular recording based monitoring of maturing cardiomyocytes, thereby filling a major technological gap in monitoring the maturation of cardiomyocytes in vitro.

Figure 1:
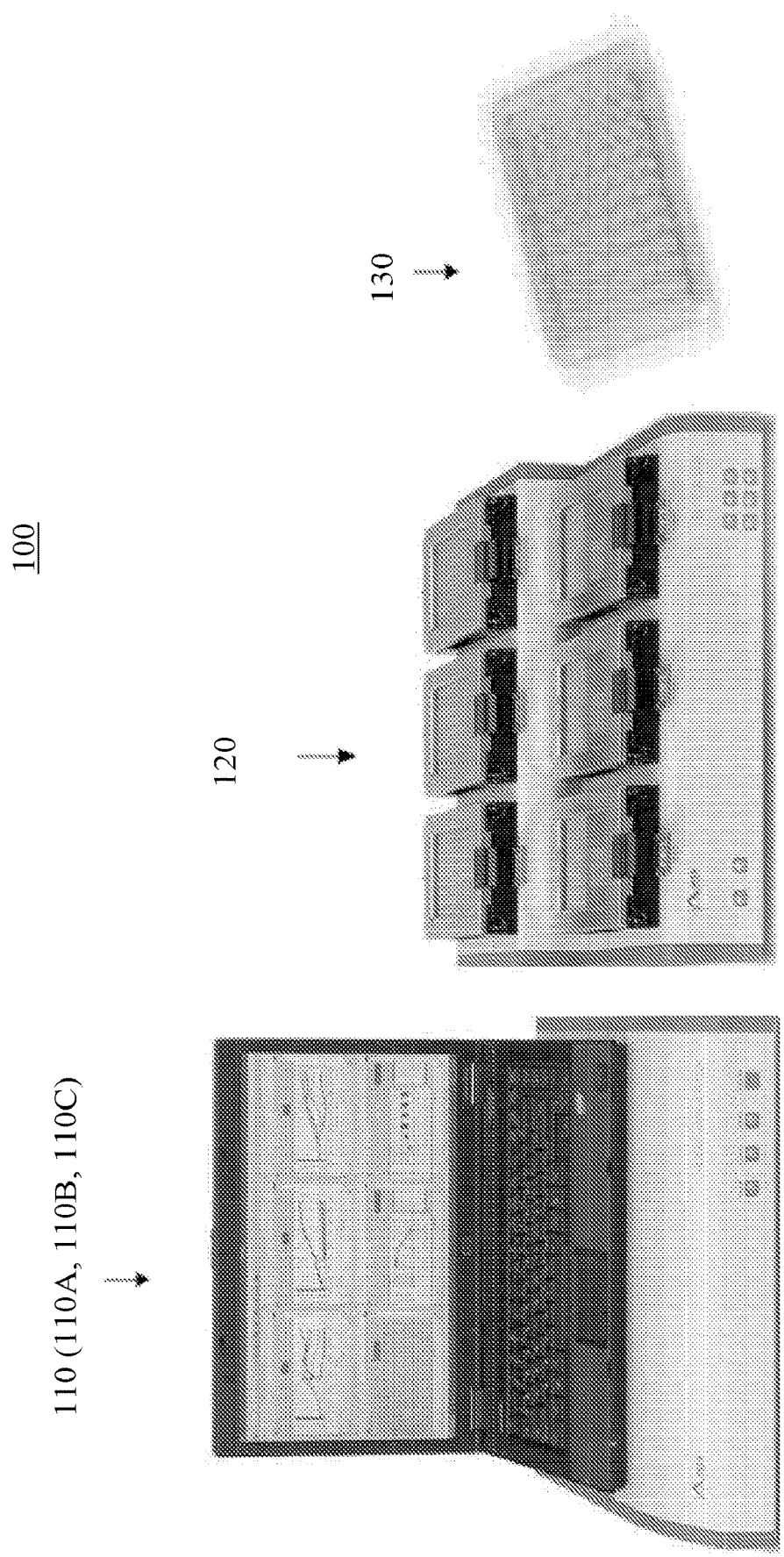
FIG. 1 depicts an exemplary system 100 for inducing and monitoring functional maturation of iPSC and ESC derived cardiomyocytes and for screening inotropic and chronotropic compounds and for compounds that affect maturation of immature cardiomyocytes, which depicts a base unit 110 housing an electronic pulse generator module 110A, integrated impedance analyzer module 110B and extracellular recording amplifier module 110C; a device station 120 embodied as an electronic multi-well plate station and cell culture devices 130 embodied as electronic plates.
Figure 2A:
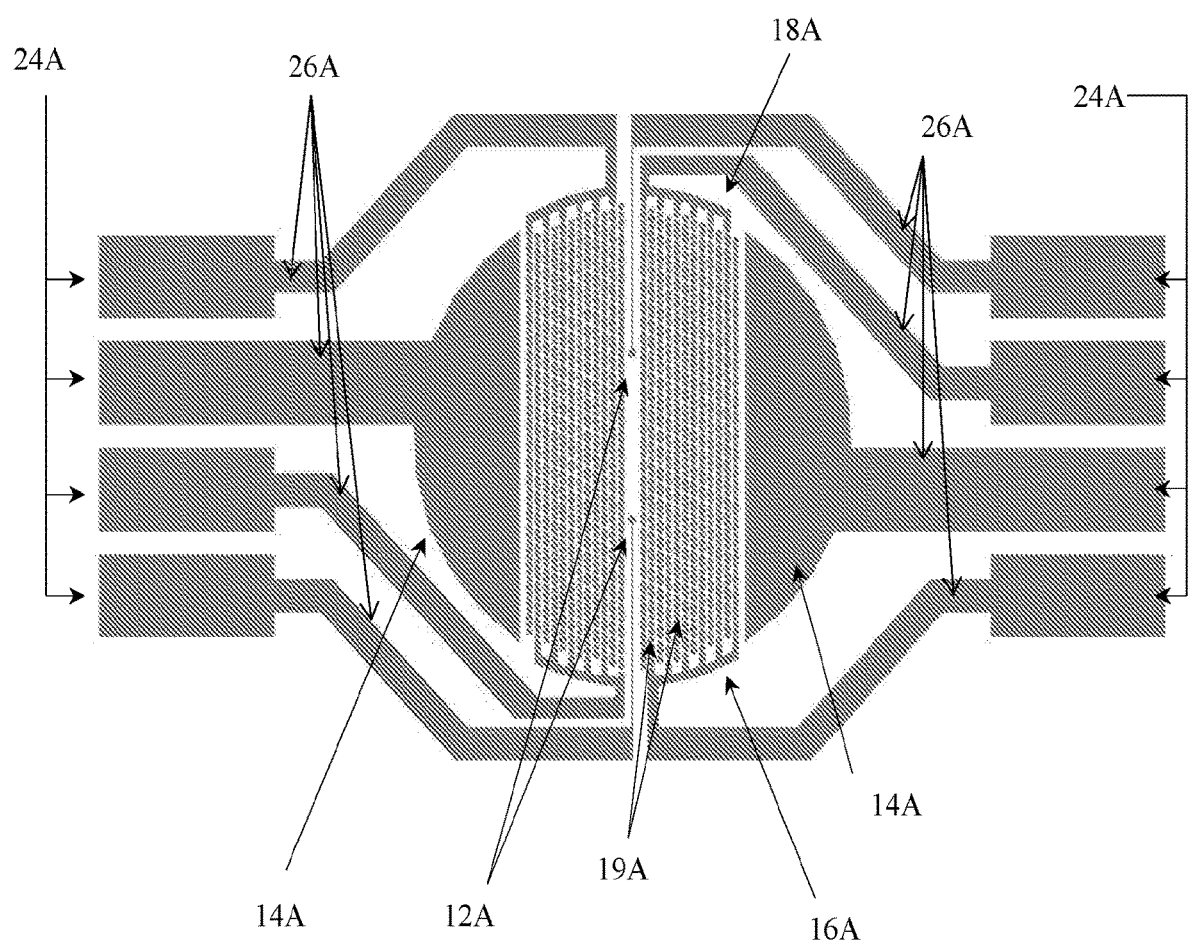
FIG. 2A depicts a schematic of an electrode configuration where the diameter of each of the two the recording electrodes 12A is 100 µm; the distance between two recording electrodes 12A is 2.98 mm; the diameter of circles in the circle-on-line electrode elements 19A is 90 µm, the center-to-center distance between two adjacent circle-on-line electrode elements 19A is 110 µm; and the gap between two shared impedance/electro-stimulation electrodes 16A, 18A and covering the recording electrodes 12A is ~290 µm. Each of the electrodes 12A, 14A, 16A, 18A are connected to a connection pad 24A via an electrical trace 26A.
Figure 2B:
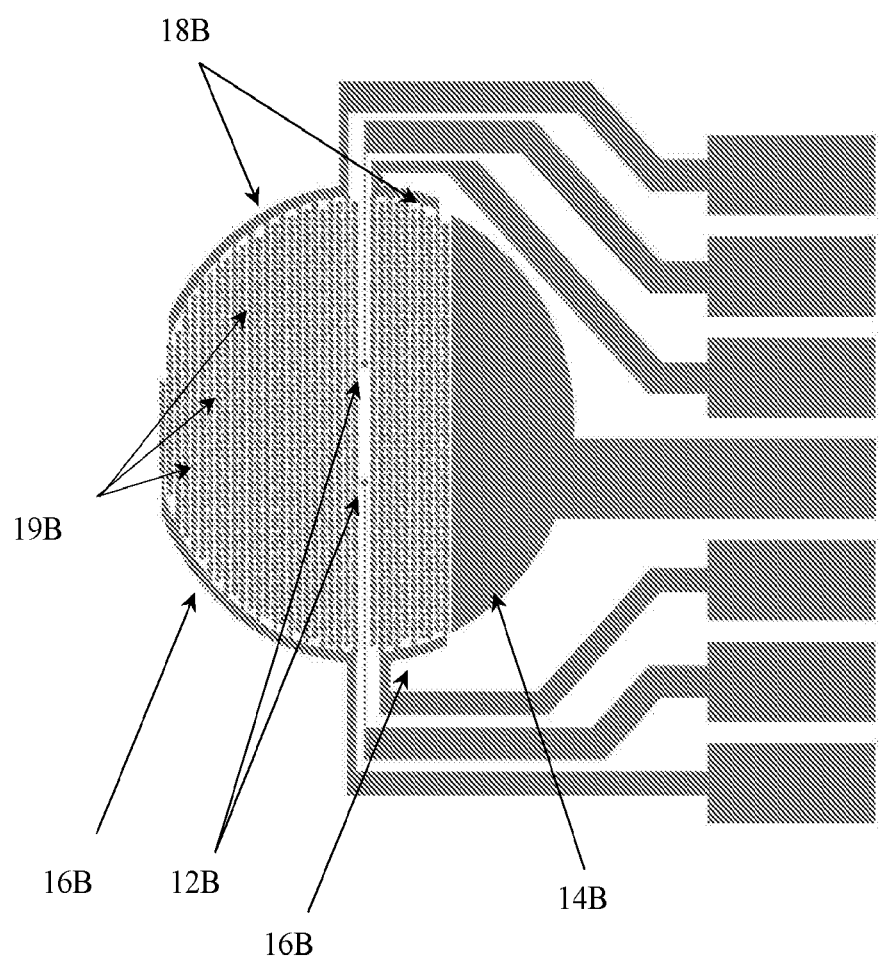
FIG. 2B depicts a schematic of an electrode configuration where each electrode array 10B includes two round-circular extracellular recording electrodes 12B and a single unitary reference electrode 14B. Electrode structures 16B, 18B are used for both electro-pulsing and cell impedance monitoring albeit at different time points by electronic switching. In this exemplary embodiment, the diameter of each recording electrode 12B is 60 um; the distance between two recording electrodes 12B is 2 mm; the diameter of circles in the circle-on-line electrode elements 19B is 90 um, the center-to-center distance between two adjacent circle-on-line electrode elements 19B is 110 um; the gap between two impedance-electrode-structures 16B, 18B and covering the recording electrodes 12B is ~290 um.
Figure 2C:
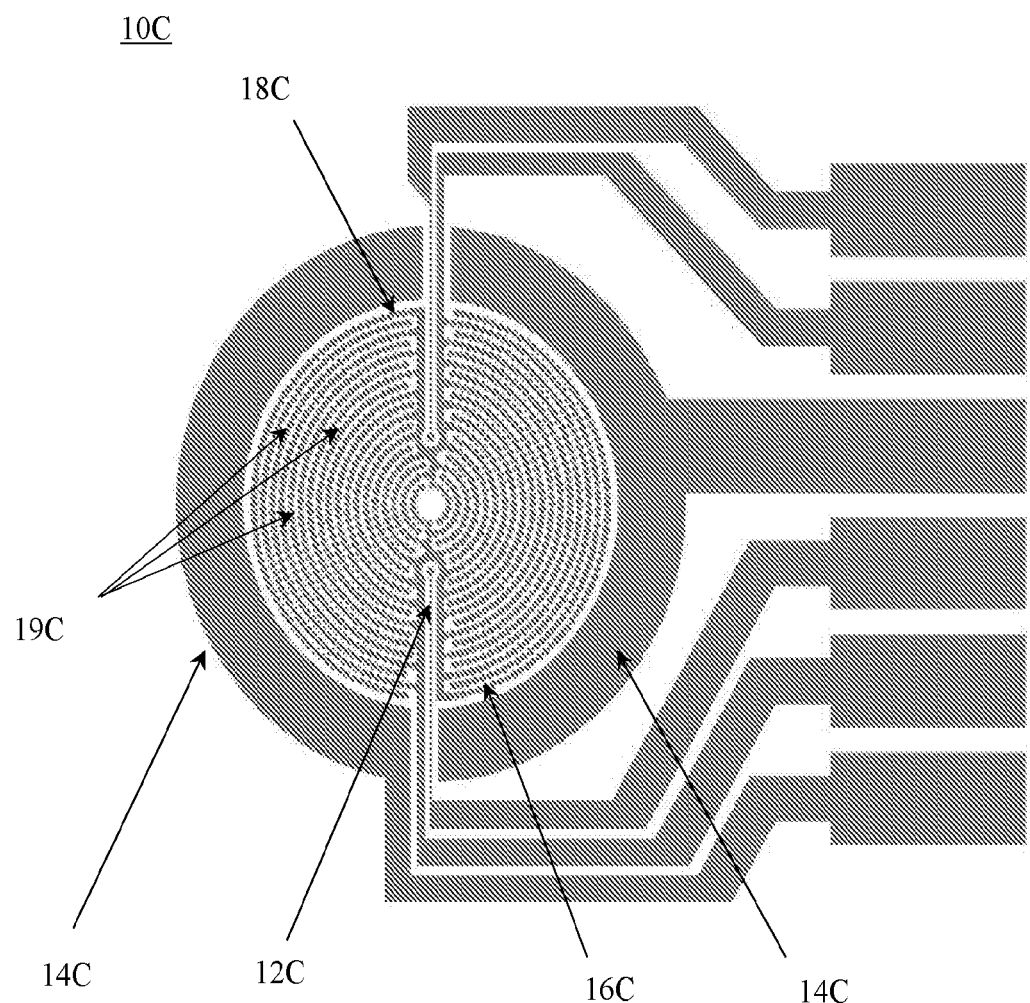
FIG. 2C depicts a schematic of an electrode configuration where each electrode array 10C is configured on a non-conductive substrate associated with a single well. The electrode array 10C includes a round-circular extracellular recording electrode 12C and a unitary one-piece reference electrode 14C. Electrode structures 16C, 18C perform both impedance measurement and electro-pulsing of cells at different time points by electronic switching. In this example, a plurality of circle-on-circular-line electrode elements 19C form interdigitated electrode structures 16C, 18C. In this exemplary embodiment, the diameter of the recording electrodes 12C is 80 um; the distance between two recording electrodes 12C is 1.44 mm; the diameter of circles in the circle-on-line electrode elements 19C is 90 um, the center-to-center distance between two adjacent circle-on-line electrode elements 19C is 110 um.
Figure 2D:
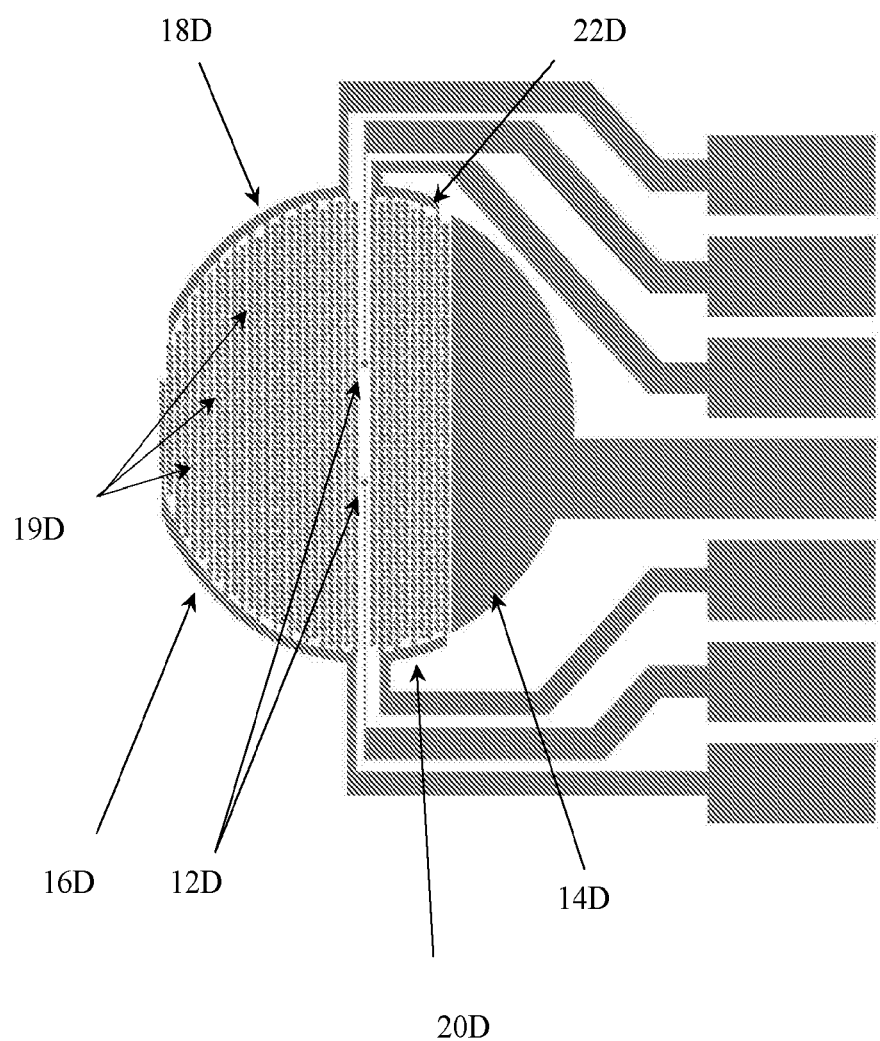
FIG. 2D depicts a schematic where an electrode array 10D includes two round-circular extra-cellular recording electrodes 12D and a single unitary reference electrode 14D. Electrode structures 16D, 18D are used for cell impedance monitoring. Electrode Structures 20D, 22D are used for electro-pulsing and for cell impedance monitoring. In this exemplary embodiment, the diameter of each recording electrode 12D is 60 um; the distance between two recording electrodes 12D is 2 mm; the diameter of circles in the circle-on-line electrode elements 19D is 90 um, the center-to-center distance between two adjacent circle-on-line electrode elements 19D is 110 um; the gap between two impedance-electrode-structures 16D, 22D and covering the recording electrodes 12D is ~290 um.

With reference to FIGS. 1-2D, the systems 100 for functionally maturing immature cardiomyocytes include an electronic pulse generator 110A configured to deliver electronic pulses according to a pulse profile that induces maturation of immature cardiomyocytes; a device station 120 configured to engage a cell culture device 130 and deliver the electronic pulses from the pulse generator 110A to the engaged cell culture device 130; and a cell culture device 130 having a substrate configured to culture cells, each substrate having an electrode array 10A-D addressable by the device station 120 when engaged; and a module 110B, 110C for electrically monitoring cultured cells.

The pulse generator 110A generates and delivers electronic pulses to the device station 120, where they are routed to the cell population(s) culturing in the cell culture device 130 to electrically pace the immature cardiomyocytes. The pulses themselves can be generated and delivered having any desired wave form that induces maturation but in a preferred embodiment, the pulse generator 110A generates and delivers a pulse in a rectangular wave form. The pulse generator 110A is also capable of generating other wave forms, such as a sine wave form, a triangle wave form and/or a sawtooth wave form. The pulse duration or pulse width can also vary as needed, but is typically between about 0.1 millisecond to about 10 milliseconds, but is more often 0.1 ms to 0.2 ms. Nonlimiting examples of voltages particularly useful in iPSC maturation can be up to about 3 volts, 2 volts, but are more typically 0.7 V to 1 V.

The pulse generator 110A is programmable so that it can selectively deliver electrostimulating pulses to each electrode array 10A-D within each well independent of other electrode arrays 10A-D in other wells and so it can deliver pulses to each electrode array 10A-D simultaneously as needed. User programming can be performed by inserting raw pulse parameters or by way of preprogrammed selectable options, where the user defines one or more pulse profiles and assigns the one or more pulse profiles to one or more wells of the device 130. A "pulse profile" as used herein refers to current pulsed over a pulse duration (or width), at a pulse intensity (or voltage) and at a pulse frequency. Pulse profiles may be programmed by the user or may be preprogrammed. To this end, in some embodiments, a plurality of pulse profiles or pulse subprofiles are programmed or preprogrammed for running in series, where the series of pulse subprofiles maintain a same waveform and voltage but increase in pulse frequency. As a nonlimiting example, a pulse profile can be series of a first pulse subprofile of about 1 Hz, followed by a second pulse subprofile having frequency of about 1.5 Hz, followed by a third pulse subprofile having a frequency of about 2 Hz. Furthermore, the series may be programmed or preprogrammed to execute profiles over a predetermined time, such as, but not limited to one week per pulse subprofile.

A user programmable feature is particularly useful because as demonstrated herein, a typical experiment where iPSCs are paced to induce maturation into cardiomyocytes having a more adult-like phenotype can take upwards of about three weeks, which limits access to the device station. By providing a user programmable feature, a same electronic pulse generator 110A and device station 120 can be used to perform multiple experiments across multiple cell culture devices 130 for multiple users. Alternatively, it may be desirable to vary pulse profiles between wells of a same multi-well device 130 to study the effect of pulsing itself, such as to further modulate maturation in the presence of a test compound, such as a compound believed to drive maturation.

In a related embodiment, the pulse generator 110A is preprogrammed with instructions to assess the maturation of immature cardiomyocytes or iPSCs into cardiomyocytes and carryout pulse programming according to the assessment. That is, the system 100 can be provided with a feedback loop where cardiomyocyte pacing is adjusted according to maturation as measured electrically. In such embodiments, the pulse generator 110A is loaded with one or more beating parameters indicative of maturation (e.g. a surrogate for force-frequency relationship) for comparison to a parameter calculated from real time measurements taken during the maturation process, and the pulse profile is adjusted accordingly. That is, by forming a database of control beating parameters indicative of maturation and corresponding pulse profiles for further maturation, the system 100 is able to automatically assess the stage of maturation and adjust the cardiomyocyte pacing according to the database to further mature the cell population or signal completion of the maturation process.

Monitoring the maturation of immature cardiomyocytes or iPSCs into mature cardiomyoctyes is performed by monitoring excitation-contraction coupling of cells undergoing further maturation. Excitation-contraction coupling (ECC) is a term used to describe the physiological process of converting an electrical stimulus to a mechanical response. The process is fundamental to muscle physiology, wherein the electrical stimulus may be an action potential and the mechanical response is in the form of contraction. Excitation-contraction coupling in cardiomyocytes is typically referred to as beating. That is, cardiomyocyte beating itself corresponds to the excitation-contraction coupling of the cells.

The beating profile of a cardiomyocyte cell population (in particular its beating force-frequency relationship) was found to be an accurate predictor of its phenotype in that young immature cardiomyocytes and iPSCs tend to beat at an irregular frequency and as a synchronized beating frequency is increased by electrical stimulation, the beating amplitude or force tends to decrease. To this end, the pulse generator includes hardware and software or is coupled to a unit having suitable hardware and software to assess the excitation-contraction coupling or beating of the cell population in culture and can determine the force-frequency relationship.

Monitoring excitation-contraction coupling of cells can be performed using cell-substrate impedance, extracellular recording of cells, through a combination of cell-substrate impedance and extracellular recording, or through optical systems, such as resonant waveguide or a resonant waveguide grating sensor. Accordingly, a central base 110 housing the pulse generator 110A may also include one or more of impedance analyzer functionality, extracellular recording functionality or resonant waveguide functionality. Such functionalities may be by way of integrating required hardware and software into the pulse generator or may be by way of communicatively coupling the pulse generator 110A to a separate impedance analyzer 110B, extracellular recording amplifier 110C, optical or resonant waveguide system. Most preferably, the pulse generator 110A is integrated into a single base unit 110 that also includes at least an impedance analyzer 110B for analyzing cell-substrate impedance.

Cell substrate impedance monitoring is a noninvasive approach for monitoring living cells. As a brief overview, microelectrodes 16A-D, 18A-D having appropriate geometries are fabricated onto a substrate, such as the bottom surfaces of a multi-well plate or similar device 130, which exposes the microelectrodes 16A-D, 18A-D to inner wells of the plate/device 130. Cells are introduced into the wells, make contact with, and attach to the electrode surfaces. The presence, absence or change in attachment of cells affects the electronic and ionic passage on the electrode sensor surfaces. When there are changes to the biological status of the cells, such as morphological changes, analogue electronic readout signals are measured automatically in real time, and are converted to digital signals for processing and for analysis. Further, cell-substrate impedance monitoring at different frequencies reveals differences in cell behavior. Broadly, fluctuations in cell-substrate impedance at lower frequencies tends to reflect changes in spacing under or between cells, while fluctuations in cell-substrate impedance at higher frequencies tend to reflect changes in overall cell coverage of the electrode.

In the xCELLigence RTCA system, impedance measurements are converted to a single parameter, termed cell index. The cell index is automatically derived and provided based on measured electrode impedance values. The cell index obtained for a given well reflects: 1) how many cells are attached to the electrode surface in the well, and 2) how well cells are attached to the electrode surface in the well. Thus, the more cells of a same type in similar physiological condition attached the electrode surface, the larger the cell index. Similarly, greater cell attachment to the electrode surface (e.g., by larger contact areas by cells spread-out more to have larger contact areas, or the cells attaching tighter to electrode surfaces), the larger the cell index.

Still further, it has been found that millisecond resolution of cardiomyocyte beating converted to impedance-based parameters, such as cell index (CI) and/or cell change index (CCI), permits high resolution of a force-frequency relationship that correlates closely to maturity status of cardiomyocytes. Cell index (CI) and cell change index (CCI) have been disused in detail in U.S. Pat. Nos. 7,470,533, 7,560,269, 8,026,080, 8,263,375, 9,612,234, and elsewhere. As such, in preferred embodiments, the pulse generator 110A is loaded with software or communicatively attached to a computer configured to calculate cell index (CI) for one or more time points for one or more wells of the multi-well device through suitable programming. In some preferred embodiments, the software can also calculate cell change index (CCI) from impedance measurements of one or more wells of the multi-well device. The software can preferably generate plots of impedance-based parameters over time, such as but not limited to impedance-based curves selected from impedance measurements, CI, or CCI that map beating force and beating frequency. The software may perform other analysis as well, such as calculate cell number from CI, generate dose-response curves based on impedance data, calculate IC values based on impedance values, and calculate kinetic parameters of the excitation cycle cell based on impedance-based parameters and impedance-based curves. Nonlimiting examples of methods for calculating and comparing beating parameters can be found in U.S. Pat. No. 9,612,234 and Examples I and II.

Monitoring excitation-contraction coupling can also be measured, at least in part, using extracellular recording of cells. In extracellular recording, an extracellular recording amplifier 110C is communicatively coupled to an extracellular recording electrode pair 12A-D, 14A-D on the substrate to permit amplifying and recording electrical voltage signals between recording electrode 12A-D and reference electrode 14A-D. That is, extracellular voltage signals are recorded as the difference in the electrical potentials between the recording electrode 12A-D and reference electrode 14A-D. Such electrical voltages are induced on the electrodes 12A-D, 14A-D as a result of ionic current or movement through cell culture media or solution as a result of opening and/or closing of different ion channels across cell membranes during the action potential duration. Extracellular recording of cardiomyocyte populations is discussed in detail in U.S. Pat. No. 9,612,234 and US 2011/0039294.

The system 100 also includes a device station 120 configured to engage one or more cell culture devices 130 so that electronic pulses can be delivered from the pulse generator 110A to the cell culture device 130 for pacing cardiomyocytes. The device station 120 is also preferably configured for placement in an incubator or has temperature and/or humidity controls to encourage cell growth and/or differentiation. In some embodiments, the device station 120 is configured to engage a cell culture device 130 embodied as a flask. In preferred embodiments the device station 120 includes one or more platforms or one or more slots for positioning one or more multi-well devices 130. The one or more platforms or one or more slots can include sockets, pins or other electrically conductive structures for electrically connecting the device 130 to the device station 120 such as interaction through connection pads 24A. The system 100 can be configured sufficiently portable such that multi-well devices 130 can be positioned in a tissue culture incubator during electro-stimulation, extracellular recording or impedance monitoring.

The device station 120 can also include electronic circuitry for connection to the electronic pulse generator and can incorporate electronic switches that can switch on and off connections to each electrode array 10A-D within the multi-well devices 130 used in the system 100. The switches of the device station 120 can be controlled by a software program within the pulse generator 110A.

The cell culture device 130 is configured to culture cells as well as to deliver and receive electrical signals. This is accomplished by providing a chamber-like housing with a suitable electrode sensor 10A-D. The sensor 10A-D is configured to deliver electrical pulses to cultured cells and to detect changes in beating frequency and amplitude though cell-substrate impedance measurement and/or extracellular recording of cells. Examples of such configurations are demonstrated in FIGS. 2A-D.

Preferably, the device 130 includes two or more wells; however, again the device 130 may have any number of wells as desired for the particular experiment. For instance, the device may have 1 well, 2 wells, 3 wells, 6 wells, 8 wells, 12 wells, 24 wells, 36 wells, 96 wells, 384 wells, or others. Preferably, well diameters are from about 1 millimeter to about 20 millimeters, more preferably from about 2 millimeters to about 8 millimeters at the bottom of the well (the end disposed on the substrate). The wells can have a uniform diameter or can taper toward the bottom so that the diameter of the well at the end in contact with the base substrate is smaller than the diameter of the opposing end.

The surface of the substrate is suitable for cell attachment and growth of cells.

Preferably, the nonconducting substrate is planar, and is flat or approximately flat. The substrate may be constructed from a variety of nonconductive materials known in the present art, including, but not limited to, silicon dioxide on silicon, silicon-on-insulator (SOI) wafer, glass (e.g., quartz glass, lead glass or borosilicate glass), sapphire, ceramics, polymer, fiber glass, plastics, e.g., polyimide (e.g. Kapton, polyimide film supplied by DuPont), polystyrene, polycarbonate, polyvinyl chloride, polyester, polypropylene and urea resin. Preferably, the substrate is biocompatible with excitable cells such as iPSCs and cardiomyocytes; however, materials that are not biocompatible can be made biocompatible by applying a biocompatible or biomolecular coating with a suitable material, such as a biocompatible polymer or others.

The substrate may be rigid but in other embodiments the substrate has an elastic modulus from 1 kPa to 50 kPa, from 5 kPa to 15 kPa, from 8 kPa to 12 kPa, or 10 kPa, which is near the stiffness of the native myocardium. Such substrates can be formed following the teachings of Jacot et al (2008), such as by polymerizing a 3%-7% acrylamide solution over a glass coverslip then coating the gel with 0.5 mg/mL collagen bound through heterobifunctional crosslinker N-sulfosuccinimidyl-6-[4'-azido-2'-nitrophenylamino] hexanoate (sulfo-SANPAH, Pierce Biotechnology, Rockville, Ill.). The tensile elastic modulus can be measured by calculating the slope of the stress-strain curve found by hanging weights from a 15 mm thick cylinder of gel. Jacot et al. (2008).

In some embodiments, the substrate includes at least one patterned island to improve cardiomyocyte alignment. As a nonlimiting example, the substrate can be patterned by adding a polymer film (such as polyacrylamide doped with acryl-NHS) and stamping fibronectin to the gel surface via poly(dimethylsiloxane)(PDMS) to form covalently bound fibronectin islands of about 50 µm×50 µm. In such embodiments, it may be preferred to isolate the patterned islands with the cytophobic acrylamide. Further guidance for patterning islands can be found in Werley et al (2017).

To improve efficiency of production, electrodes 12A-D, 14A-D, 16A-D, 18A-D, 20D, 22D of the invention may be applied to the substrate followed by joining the electrode 12A-D, 14A-D, 16A-D, 18A-D, 20D, 22D applied substrate to a plate of bottomless wells or may be applied to a well already having the substrate as a bottom. Electrodes 12A-D, 14A-D, 16A-D, 18A-D, 20D, 22D may be formed from larger sheets of conductive metal, such as via laser ablation of a metallic film and may be applied directly to the substrate. Alternatively, electrodes 12A-D, 14A-D, 16A-D, 18A-D, 20D, 22D may be printed on the substrate using printing techniques such as those similar to ink-jet printing where a conductive fluid having ultraviolet (UV) curable monomers, polymers or compounds is printed on the substrate, then a light source is applied to cure the applied conductive fluid to form electrodes. The skilled artisan will appreciate that conductive material may be applied directly to a planar substrate or may be inserted into grooves laser ablated or formed into the substrate surface. A glue, such as a UV curable glue, can be applied between the substrate and electrode or above the electrode for added security. Further, when applying conductive fluids, it may be preferred to apply a mask prior to applying the fluid to further define the electrode area.

The electrode sensor 10A-D is an electrode array configured to deliver an electric pulse to cells on the substrate and configured to monitor the beating of cells. Beating is monitored using cell-substrate impedance monitoring and/or extracellular recording of cells. Examples of suitable electrode 12A-D, 14A-D, 16A-D, 18A-D, 20D, 22D configurations are shown in FIGS. 2A-2D.

In some embodiments, the device includes separate electrodes for each function. For example, in some embodiments the device includes electrodes for electrostimulating cells, different electrodes for monitoring cell substrate impedance of cells attached to the substrate, and still different electrodes for extracellular recording of cells. In other embodiments, electrodes are shared between different functional pairs. As an example, one electrode within a pair of electrostimulating electrodes is shared with another electrode to function as a cell-substrate impedance monitoring electrode pair or with another electrode to function as an extracellular recording electrode pair.

In still other embodiments, a same electrode pair performs two distinction functions. As an example, a pair of cell-substrate impedance monitoring electrodes can be used for electro-stimulation when not measuring impedance.

Preferably electrodes 12A-D, 14A-D, 16A-D, 18A-D, 20D, 22D within each well of the device are individually addressed, meaning that electrical traces 26A and connection pads 24A of the arrays are configured such that each array can be independently connected to the device station 120 and electronic pulse generator 110A so that each electrode pair can be operated independently of other electrode pairs in other electrode wells. This permits each well within the device 130 to be independently monitored and electro-stimulated as needed.

Electrical traces 26A of conductive material used to connect each of the electrodes 12A-D, 14A-D, 16A-D, 18A-D, 20D, 22D to a corresponding connection pad 24A can be fabricated of any electrically conductive material. The traces 26A can be localized to the surface of the substrate, and can be optionally covered with an insulating layer. Alternatively the traces can be disposed in a second plane of the substrate.

Turning now to the pair of cell-substrate impedance monitoring electrodes 16A-D, 18A-D, each pair includes two or more electrode structures that are constructed to have dimensions and spacing such that they can, when connected to an impedance analyzer, operate as a unit to generate an electrical field in the region of spaces around the impedance electrode structures. In preferred embodiments, the pair of impedance electrodes 16A-D, 18A-D includes two impedance measurement electrode structures, each of which includes multiple electrode elements 19A, or substructures, which branch from the electrode structure. In preferred embodiments, the electrode structures within each pair have substantially the same surface area.

Preferred arrangements for electrode elements 19A that form the pair of impedance monitoring electrodes 16A-D, 18A-D and gaps between the electrodes 16A-D, 18A-D and electrode buses in a given pair are used to allow all cells, no matter where they land and attach to the pair of impedance measurement electrodes to contribute similarly to the total impedance change measured for the pair. Thus, it is desirable to have similar electric field strengths at any two locations within any given pair of impedance measurement electrodes 16A-D, 18A-D when a measurement voltage is applied to the pair. At any given location of the pair, the field strength is related to the potential difference between the nearest point on a first electrode structure of the pair and the nearest point on a second electrode structure of the pair. It is therefore desirable to have similar electric potential drops across the electrode elements 19A and across the electrode buses of a given pair. Based on this requirement, it is preferred to have an approximately uniform electrode resistance distribution across the whole pair where the electrode resistance at a location of interest is equal to the sum of the electrode resistance between the nearest point on a first electrode structure (that is the point on the first electrode structure nearest the location of interest) and a first connection pad connected to the first electrode structure and the electrode resistance between the nearest point on a second electrode structure (that is the point on the first electrode structure nearest the location of interest) and a second connection pad connected to the second electrode structure.

Achieving an approximately uniform distribution across the pair of impedance measurement electrodes 16A-D, 18A-D can be achieved, for example, by having electrode structures and electrode buses of particular spacing and dimensions (lengths, widths, thicknesses and geometrical shapes) such that the resistance at any single location on the pair is approximately equal to the resistance at any single other location on the pair. In most embodiments, the electrode elements (or electrode structures) of a given pair will have even spacing and be of similar thicknesses and widths, the electrode buses of a given pair will be of similar thicknesses and widths, and the electrode traces 26A leading from a given pair to a connection pad 24A will be of closely similar thicknesses and widths. Thus, in these preferred embodiments, a pair of electrode structures is designed such that the lengths and geometrical shapes of electrode elements or structures, the lengths and geometrical shapes of electrode traces, and the lengths and geometrical shapes of buses allow for approximately uniform electrode resistance distribution across the pair.

When incorporating configurations having two or more wells, impedance measurement electrodes 16A-D, 18A-D between electrode arrays 10A-D of different wells can be entirely independent of one another by connection to entirely separate connection pads 24A or can share a common connection pad 24A. For example one of the impedance measurement electrode structures of a first well can be connected to a connection pad 24A that also connects to an impedance measurement electrode structure of another well.

Moving on to the extracellular recording electrodes 12A-D, 14A-D generally, extracellular recording is conducted by amplifying and recording electrical voltage signals between a recording electrode(s) 12A-D and reference electrode(s) 14A-D. In order to achieve improved consistency and reproducibility of the recorded voltage signals, it is desirable to minimize the contribution of any electrical signal from the reference electrode 14A-D to the recorded voltage signals and to ensure that the majority, if not all, of the recording voltage signals are derived from the recording electrode 12A-D. Thus, generally, it is desirable and it is recognized for the reference electrodes 14A-D to have small electrode impedances. The small electrode impedance is achieved by using reference electrodes 14A-D with large effective surface areas by increasing the ratio of the surface area of the reference electrodes 14A-D to that of recording electrode 12A-D by a factor of a hundred, even thousands of times.

The reference electrode 14A-D generally, can be a unitary or unbranched electrode and may be of a simple geometry such as a circle, a square or others. In other embodiments, the reference electrode 14A-D has a branched configuration, which may result in a large surface for the reference electrode. In some embodiments, the ratio of the surface area of the reference electrode 14A-D to that of the recording electrode 12A-D is more than 2. In other embodiments, the ratio of the surface area of the reference electrode 14A-D to that of the recording electrode 12A-D is 10 or more than 10. In still other embodiments, the ratio of the surface area of the reference electrode 14A-D to that of the recording electrode 12A-D is 100 or more than 100. In other embodiments the ratio of the surface area of the reference electrode 14A-D to that of the recording electrode 12A-D is 1000 or more than 1000. In other the ratio of the surface area of the reference electrode 14A-D to that of the recording electrode 12A-D is 10,000 or more than 10,000.

In some embodiments the device 130 simultaneously measures impedance and performs extracellular recording. However, some devices 130 do not perform simultaneous impedance monitoring and extracellular recording, but instead share one or both electrodes between the pair of impedance measurement electrodes with the extracellular recording electrode pair. When using impedance electrodes in the form of interdigated electrode structures having a plurality of electrode elements, typically the shared electrode would be used as a reference electrode in the extracellular recording electrode pair. This can be accomplished when the surface area of the impedance monitoring electrode(s) is sufficiently larger than the surface area of the recording electrode to act as a reference electrode. The skilled artisan will appreciate that by electrically switching a pair of interdigated impedance electrodes from impedance monitoring to function as a single reference electrode, the surface area ratio of the combined interdigated electrodes to recording electrode would substantially increase and thus may be preferable in some instances. Further, it is also possible, though not preferred to utilize an impedance measurement electrode as a recording electrode when the reference electrode is sufficiently larger than the impedance measurement electrode. While not preferred this approach is more likely when using impedance measurement electrode configurations having a small working electrode and large counter electrode as previously detailed in the art.

Figure 5:
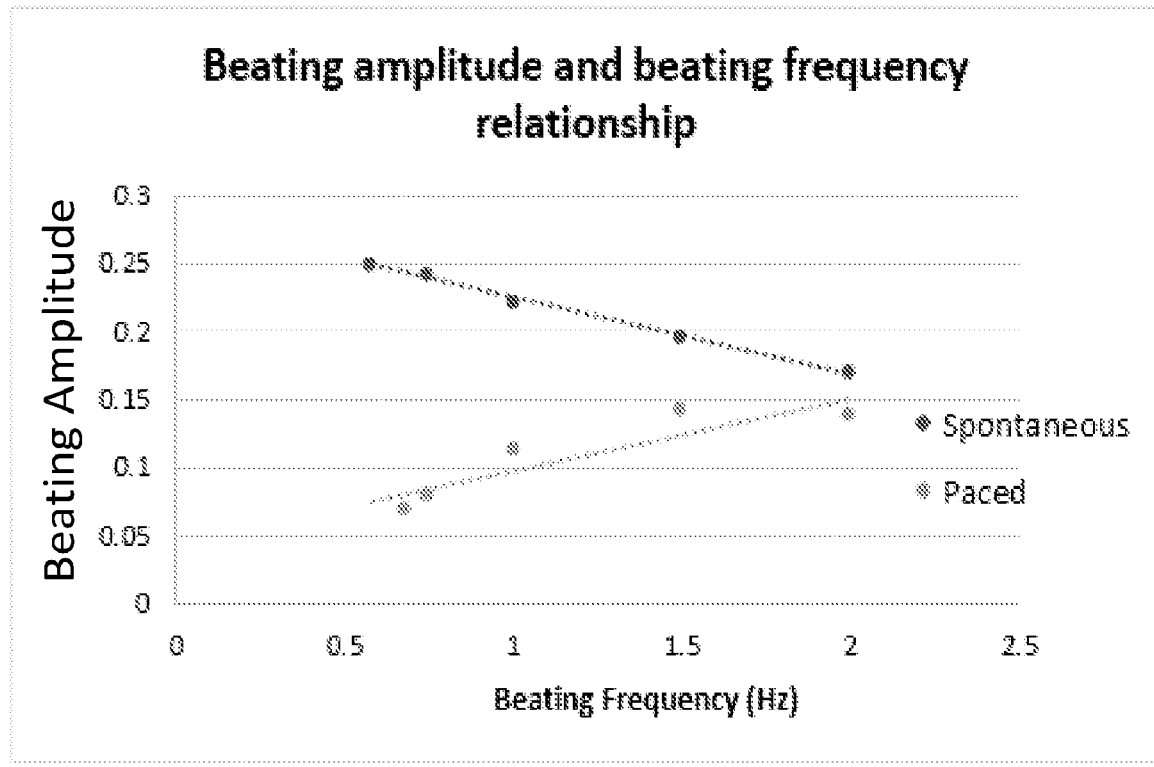
FIG. 5 is a graph comparing beating amplitude vs beating frequency of electrically paced cardiomyocytes compared to spontaneously beating cardiomyocytes showing increasing beating amplitude (beating force) as electric pacing frequency is increased. Here the force-frequency relationship increases in paced cells and decreases in spontaneously beating cells.

B. Functional Maturation of Immature Cardiomyocytes Derived from Pluripotent Stem Cells (iPSC) Using Electrostimulation It has been shown that iPSC cardiomyocytes often display an immature or embryonic phenotype as evidenced by gene expression analysis, structural studies and functional studies. One of the hallmarks of the immature phenotype of iPSC cardiomyocytes is a negative force-frequency relationship where increased beating rate does not increase amplitude or beating force. Rather, as shown in FIG. 5, the amplitude or beating force tends to reduce or weaken. To this end, the invention provides methods of monitoring this force-frequency relationship and pairs it with methods developed to induce further maturation of iPSC derived cardiomyocytes and ESC derived cardiomyocytes into cardiomyocytes having a more mature or adult-like phenotype. In particular, the systems and methods herein not only induce functional maturation of iPSC and ESC derived cardiomyocytes but also electrically monitor maturation by measuring beating amplitude and calculating the force-frequency relationship. The result is a population of functionally maturing cardiomyocytes that respond appropriately in a positive force-frequency relationship, which can then be used for subsequent testing of inotropic and chronotropic compounds or to study the maturation process.

In view of the above, a method of maturing functionally immature cardiomyocytes is provided, the method including: providing a system, preferably having an electrode sensor array, wherein the system is configured to culture, electrically pace, and monitor beating of beating cells; culturing immature cardiomyocytes in the system; monitoring the immature cardiomyocytes to characterize cardiomyocyte beating as synchronized or not synchronized; and if synchronized, electrically pacing the immature cardiomyocytes according to a pulse profile until the immature cardiomyocytes mature into functionally adult cardiomyocytes.

As with the systems 100 described above and briefly reference to FIGS. 1-2D, an impedance monitoring electrode array 16A-D, 18A-D can be positioned on a substrate and can be operably connected to an impedance analyzer 110B to monitor cell-substrate impedance of a cell population cultured in the system 100. Alternatively, an extracellular recording electrode array 12A-D, 14A-D can be operably connected to an extracellular recording amplifier 110C to conduct extracellular recording of a cell population cultured in the system. Still further, the system 100 can include an impedance monitoring electrode array 16A-D, 18A-D on a substrate, an extracellular recording electrode array 12A-D, 14A-D on the substrate, an impedance analyzer 110B, and an extracellular recording amplifier 110C, where the system 100 is configured to monitor cell-substrate impedance and conduct extracellular recording of a cell population cultured in the system 100.

As a nonlimiting example, the methods can be conducted using the xCELLigence RTCA CardioECR system (ACEA Biosciences, Inc. San Diego, Calif.), which is depicted in FIG. 1, by: seeding iPSC derived cardiomyocytes in wells of the CardioECR Plate (E-Plate CardioECR 48) at an appropriate density; allowing the cells to attach, grow and achieve spontaneous beating rhythm while continuously monitoring the spontaneous beating activity using the CardioECR system; and performing directed electrical pacing of the iPSC derived cardiomyocytes after spontaneous, synchronously beating is observed for the cardiomyocyte monolayer, over the course of 4 weeks post-seeding while continually monitoring beating activity.

The skilled artisan will appreciate that the methods can be used to differentiate various cardiomyocyte precursor cells. In particular, the methods can be used to further differentiate iPSCs or ESCs already partially differentiated into immature cardiomyocyte cells. Conceptually, the differentiation of ESCs into terminally differentiated cardiomyocytes is no different than that of iPSCs. The differentiation of both relies on modulating signaling pathways that guide embryonic development in vivo (Activin/Nodal, TGFβ, GSK3, Wnt, BMP, etc) and follow the same general procedures. Moran et al. (2010). Cardiomyocytes derived from PSCs can begin contracting after seven days of differentiation. Moran et al. (2010). However, as already eluded to, such PSCs have an immature phenotype. Immature cardiomyocytes compared to mature cardiomyocytes tend to differ in gene expression profile, and differ in action potential profile. Moran et al. (2010). Thus, determining whether cardiomyocytes are immature can be by way of gene expression analysis, or more preferably using the electric monitoring approach described herein. In particular, cell-substrate impedance monitoring and/or extracellular recording can be used to assess the beating frequency, contractility, beating amplitude, and action potential. Further, the force-frequency relationship can then be evaluated by comparing the beating amplitude over an increasing beating frequency (induced by pacing). An increasing beating amplitude that follows increasing frequency is indicative of mature cardiomyocytes; whereas a decreasing beating amplitude that follows increasing frequency is indicative of immature cardiomyocytes. As such, cardiomyocytes can be electrically tested whether they have an adult phenotype or an immature phenotype by assaying the beating amplitude over an increasing beating frequency. This testing can be performed at different periods throughout the maturation process to assess maturation or as feedback to adjust pulsing frequency.

For completeness, the method is not limited to any particular species, but the methods will most often use a cell from a same species that is to ultimately be diagnosed or treated with a therapeutic. To this end, when conducting assays that may lead to the treatment of a human, such as for the treatment of a heart disorder, most often human iPSCs will be used. When conducting studies for veterinary medicine, most often iPSCs or ESCs from a same species that is to be diagnosed or treated will be used. Still further, when the object is to diagnose or treat a human patient, most preferably the iPSCs will be from cells collected from the same patient that is to be treated or diagnosed.

The methods of the invention are further desirable in that they do not require a special cell culture media. Conventional cell culture media can be used. However, the system can also be used with specialized media that may further facilitate maturation in addition to electrical pacing.

While the methods provide for the further differentiation of immature cardiomyocytes, the initial differentiation procedures can also be conducted on the cell cultured device and electrically monitored. In addition, coatings used in the differentiation of iPSCs into mature cardiomyocytes may also be applied to the cell culture device and corresponding procedures performed.

Still further, in some embodiments, maturation of immature cardiomyocytes is performed with the immature cardiomyocytes aligned on patterned substrates. As a nonlimiting example, culturing cardiomyocytes on patterned islands of fibronectin separated by bare polyacrylamide, which is cytophobic, was shown to improve spontaneous beating. Werley et al. (2017). As such, the methods herein may include culturing immature cardiomyocytes on patterned substrates, such as, but not limited to fibronectin patterns as taught or suggested in Werley et al, with the addition of the electrodes for pulsing and electrically monitoring cardiomyocytes. That is, the devices for iPSC maturation can be patterned to further drive maturation.

In some embodiments, the immature cardiomyocytes are cultured on a substrate having an elastic modulus from 1 kPa to 50 kPa, 5 kPa to 15 kPa, 8 kPa to 12 kPa, or 10 kPa, which is near the stiffness of the native myocardium. Such substrates can be formed following the teachings of Jacot et al (2008) with the addition of electrodes for pulsing and electrically monitoring cardiomyocytes. That is, the devices for iPSC maturation can have an elastic modulus that mimics the myocardium.

In some embodiments, the immature cardiomyocytes are cultured in the presence of a vascular-like network. As a nonlimiting example, the immature cardiomyocytes are seeded on a vascular network of endothelial cells (ECs). Vascular ECs produce a variety of auto- and paracrine agents including VEGF, angiopoietin and nitric oxide that influence cardiomyocyte metabolism, growth, contractility, and rhythmicity of the heart. Brustaert (2003). In other embodiments, the immature cardiomyocytes are seeded on a vascular network of fibroblasts. In other embodiments, the immature cardiomyocytes are seeded on a vascular network of human umbilical vein endothelial cells (HUVEC) and human adipose stromal cells (hASC). Adipose stromal cells (hASCs) have been shown to produce significant amounts of angiogeneic factors and cytokines including VEGF, hepatocyte growth factors and angiopoietin. In other embodiments, the immature cardiomyocytes are seeded on a vascular network of HUVECs and human foreskin fibroblasts. Each of the above have been shown to be beneficial for culturing cardiomyocytes. Vourenpaa et al. Each can be used with the methods and systems herein.

Figure 3:
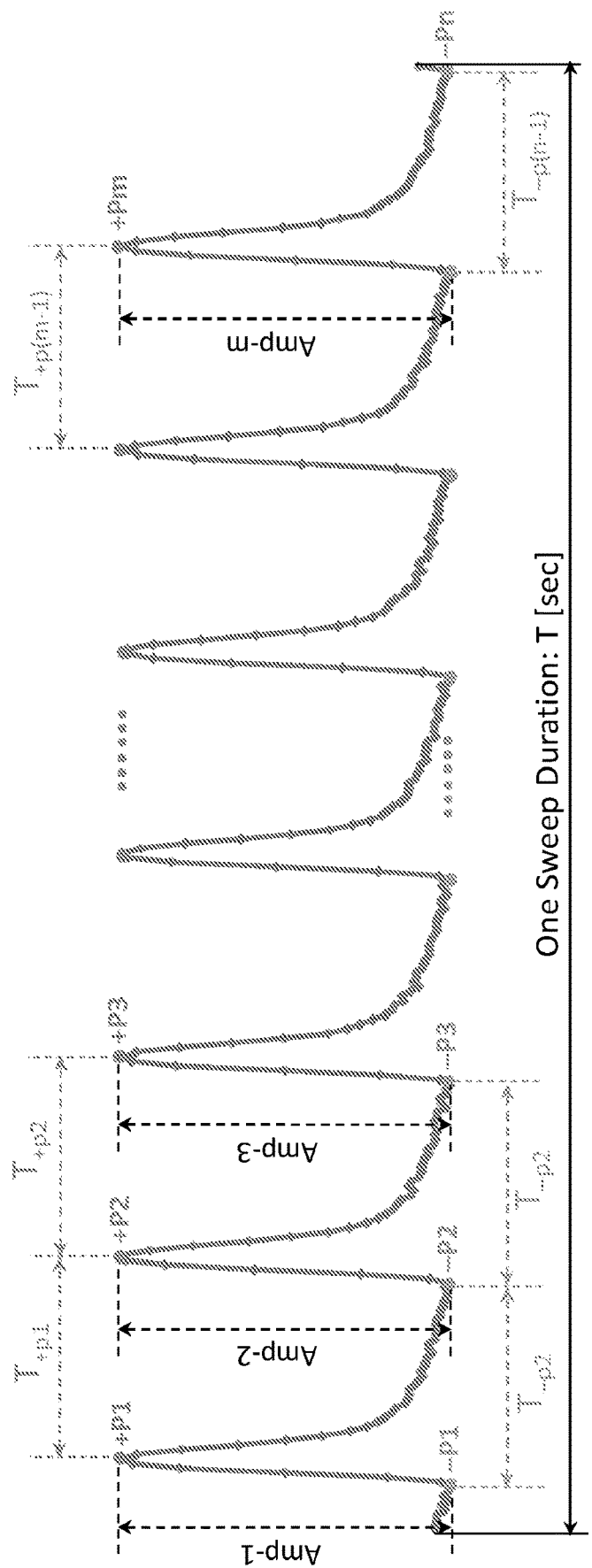
FIG. 3 is a graph depicting the beating cycle of cardiomyocytes having a mature or adult like phenotype.

Returning to the electric monitoring of immature cardiomyocytes to determine whether or not beating is synchronized, it is preferred that the cells synchronize in beating prior to executing a pulse profile that will further differentiate the immature cardiomyocytes into mature cardiomyocytes. Electric monitoring can include monitoring cell-substrate impedance of the immature cardiomyocytes, extracellular recording of the immature cardiomyocytes, or both. More preferably, whether beating is synchronized is determined by cell-substrate impedance monitoring to obtain a beating parameter, whether raw impedance value or cell index, then compared over time. In particular determining whether beating is synchronized is by way of determining a beating rate (also referred to as "beating frequency") and comparing the beating rate over time. That is, a population that is not synchronized in beating will not generate a continuous and reproducible impedance-based curve. Nor will the beating culture produce a reproducible beating peak (FIG. 3 depicts a series of beating peaks). Rather the curve will shift or lack refinement. Beating is monitored until synchronized, which is typically about 4 days to a few weeks.

It has been found that synchronized beating can be achieved faster by electrically pacing the immature cardiomyocytes. That is, if the cardiomyocyte beating is not synchronized, the method can also include electrically pacing the immature cardiomyocytes until cardiomyocyte beating is synchronized. Compared to the pulse profiles used for differentiation, electrically pacing the cardiomyocytes to synchronize beating typically maintains a slower pulse frequency. That is, immature cardiomyocytes can be slowly but steadily paced until beating is synchronized. Typically, the pacing is at a constant frequency. Most preferably, the pacing is at the same pace as the beating rate of the immature cardiomyocytes in culture. This frequency is typically about 0.5 Hz to about 1 Hz but can also be slower such as 0.5 Hz, 0.1 Hz, 0.2 Hz, 0.3 Hz or 0.4 Hz. A diseased genotype/phenotype may have a slow beating rate (e.g. 0.5 Hz-0.5 Hz).

Once beating is synchronized, the method includes electrically delivering a pulse profile to the immature cardiomyocytes that induces further differentiation. That is, an appropriately-chosen pulse intensity or amplitude is used to pace or stimulate the immature cardiomyocytes at a pulse frequency to drive maturation. The pulse intensity should be sufficiently high to result in pacing of the cardiomyocytes (i.e. each applied pulse could lead to a beating cycle of the cardiomyocytes in the well). On the other hand, the pulse intensity or amplitude shall be within a range since a very high field intensity may cause undesired effects on the cardiomyocytes. For example, when the pulse intensity is too high, there could be water-electrolysis occurring on the electrodes, leading the change in the local pH as well as O2 and/or H2 bubbling in the cell culture media, and causing undesired physiological effects on cardiomyocytes. The exact pulse intensity range that effectively paces cardiomyocytes in any given experimental condition may also depend on the electrode geometry used in the wells of the device. For example, electrode arrays with larger spacing between neighboring electrodes would require larger pulse intensities than those with smaller spacing for achieving the same pacing effects. For example, large pulse intensities up to a few volts (e.g. 3 V), or even higher, may be needed for the electrode geometries having larger distances between neighboring electrodes.

An exemplary pulse profile has a pulse duration or width from 0.1 milliseconds to 0.2 milliseconds with duration up to 10 milliseconds being acceptable. An appropriately-chosen pulse duration shall be used to pace or stimulate cardiomyocytes. With appropriately applied pulse intensity, pulse duration should be sufficiently long to result in pacing of the cardiomyocytes (i.e. each applied pulse could lead to a beating cycle of the cardiomyocytes in the well). On the other hand, the pulse duration does not have to be too long, since a too long pulse duration may cause undesired effects on the cardiomyocytes. For example, when the pulse duration is too high, there could be a large averaged, effective, direct-current DC field bias applied to the electrodes (e.g. pulse duration of 700 milliseconds for a 1 Hz, 1 V pulse would mean a DC voltage of 0.7V (=1V*700 millisecond*1 Hz) applied to the electrodes, leading to among undesired effects, water-electrolysis occurring on the electrodes and causing a change in the local pH as well as O2 and/or H2 bubbling in the cell culture media, and causing undesired physiological effects on cardiomyocytes. Generally the pulse duration should be applied as short as possible, as long as it leads to the effective pacing of the cardiomyocytes (i.e. each applied pulse could lead to a beating cycle of the cardiomyocytes in the well).

Most preferably, the pulse profile has a rectangular pulse shape and an intensity or voltage of about 0.7 V to 1 V but can also be up to about 2 volts. In other embodiments, the voltage is up to 3 volts. In some instances intensity is increased when pacing frequency is increased. The pulse duration or pulse width is generally about 0.1 milliseconds to 0.2 milliseconds but can be up to 10 milliseconds and can also increase when pacing frequency is increased.

While the pulse intensity and duration can be increased over time, accelerating the differentiation of immature cardiomyocytes is believed to be primarily due to increasing the beating rate of the cell culture, which is accomplished by increasing electric pacing. Experimentally, it was found that increasing the beating rate of the immature cardiomyocyte culture over time increases the rate of differentiation. To this end, what could take months to a year or so to accomplish is demonstrated herein to take place within weeks. To this end, differentiating immature cardiomyocytes is primarily accomplished by way of applying a pulse profile with a varying pulse frequency to pace immature cardiomyocytes over time.

The skilled artisan will appreciate that the pulse profile can vary depending on the beating rate of the immature cardiomyocytes and can also vary depending on the method used to differentiate immature cardiomyocytes into mature cardiomyocytes. As an example, a pulse profile will typically start at a frequency that matches or nearly matches the beating rate of the immature cardiomyocytes, which can vary. Most often, the pulse profile will start at a slower pulse frequency and increase in frequency over time. This initial lower pulse frequency should be appropriate so that the cardiomyocyte can follow the pacing pulses (i.e. each pacing pulse could result in one beating cycle of the cardiomyocytes in the well). Experimentally, an adult-like or mature phenotype was achieved more quickly when increasing the pacing stepwise at about 0.5 Hz increments over time until reaching final pacing frequency of 2 Hz. Surprisingly beneficial results were achieved when holding a pacing frequency at a same rate for 1 one week, then increasing the pacing by about 0.5 Hz weekly until achieving a pacing frequency of 2 Hz. However, it is expected that shorter periods, such as days, would be acceptable as would longer durations, such as weeks.

As an example, a pulse profile was developed to have a pulse frequency that varies between 0.5 Hz and 2 Hz over time. As another example, the pulse profile includes a pulse frequency that varies between 1 Hz and 2 Hz over time. As another example, the pulse profile includes a pulse frequency that increases from 0.75 Hz to 2 Hz over time. As another example, the cardiomyocytes of certain genotype or phenotype, such as a diseased genotype/phenotype, may require an initial lower pulse frequency such as 0.5 Hz, or 0.3 Hz or even lower so that the cardiomyocytes can be effectively paced. On the other hand, the pulse frequency can be increased over time from an initial low pulse rate to a higher pulse frequency such as 3 Hz, or even higher, depending on the requirement of the assays that would use such cardiomyocytes that are being paced. The skilled artisan will appreciate that the time period between increasing the pulse frequency can also vary but in some embodiments, the time period for increasing the pulse frequency occurs over 2-6 days. In other embodiments, time period for increasing the pulse frequency occurs over 1 to 5 weeks. As a nonlimiting example, further differentiation of immature cardiomyocytes can occur when pulsing at 0.75 Hz for 1 week, 1.5 Hz for another week, and 2 Hz for still another week. Preferably the increasing pulse frequency doubles in frequency over time. Cardiomyocyte maturation can be followed by periodically testing the force-frequency relationship of the beating culture to determine whether the force-frequency relationship increases, which is indicative of maturity, or decreases, which is indicative of immaturity. In particular, testing can include progressively increasing the pacing rate of the cardiomyocytes and simultaneously recording the beating amplitude, which is a surrogate for force. If there is a negative beating amplitude/electrical pacing rate relationship then the cardiomyocyte is deemed immature; whereas if there is a positive amplitude/electrical pacing rate relationship, the cardiomyocyte is deemed "mature".

Accordingly, a pulse profile to induce differentiation of immature cardiomyocytes into those with an adult phenotype can include electrically pacing cardiomyocytes by applying a pulse profile having a pulse frequency between 1 Hz and 2 Hz. Most preferably the pulse profile increases the pulse frequency over time. In embodiments, where the immature cardiomyocytes are beating at a frequency of less than 1 Hz, the pulse frequency applied may double in frequency over time. The immature cardiomyocytes are pulsed until obtaining a positive force-frequency relationship. In particular, the functionally adult cardiomyocytes have a positive force frequency; whereas immature cardiomyocytes have a negative force-frequency.

In some embodiments, a compound that drives cardiomyocyte maturation is added to the immature cardiomyocytes to help drive maturation. In some embodiments, a growth factor or a growth hormone is added to the immature cardiomyocytes. In some embodiments an angiogeneic factor is added to the immature cardiomyocytes. In some embodiments, an angiopoietin is added to the immature cardiomyocytes. Angiopoietins are a family of growth factors that includes the glycoproteins angiopoietin 1 and 2 and the ortholog 4. In other embodiments, VEGF is added.

Tri-iodo-L-thryonine (T3) is growth hormone essential for optical heart growth. Yang et al. (2014). Yang found that T3 treatment of immature cardiomyocytes increased cardiomyocyte size, increased sarcomere length, decreased proliferation, increased contractile force generation, enhanced calcium handling properties and increased maximal mitochondrial respiration capacity. As such, the addition of growth hormones may further accelerate the maturation process when coupled with electric pacing.

Figure 4:
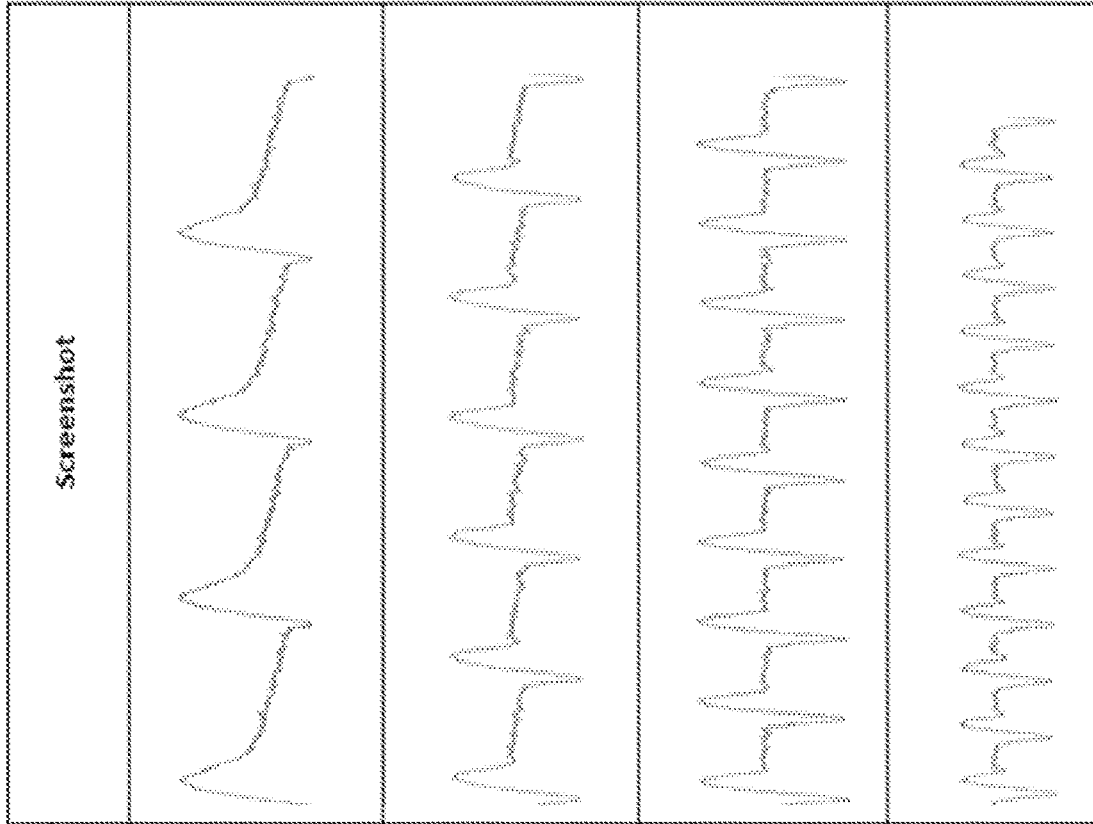
FIG. 4 is a table showing pulse settings and corresponding screenshots of beating activity recorded continuously for 6 seconds before pacing, after pacing at 1 Hz, after pacing at 1.5 Hz and after pacing at 2 Hz.

As further demonstration of the above, Example III describes the use of the xCELLigence RTCA CardioECR system to measure and monitor dynamic changes in beating activity during chronic application of electric pacing to iPSC cardiomyocytes. The cells were then tested to assess functional maturation in Example IV by electrically pacing the cells over a 40-minute interval to determine if the cells would respond in a positive force-frequency relationship. Confirming results are shown in FIGS. 4-5.

Figure 6A:
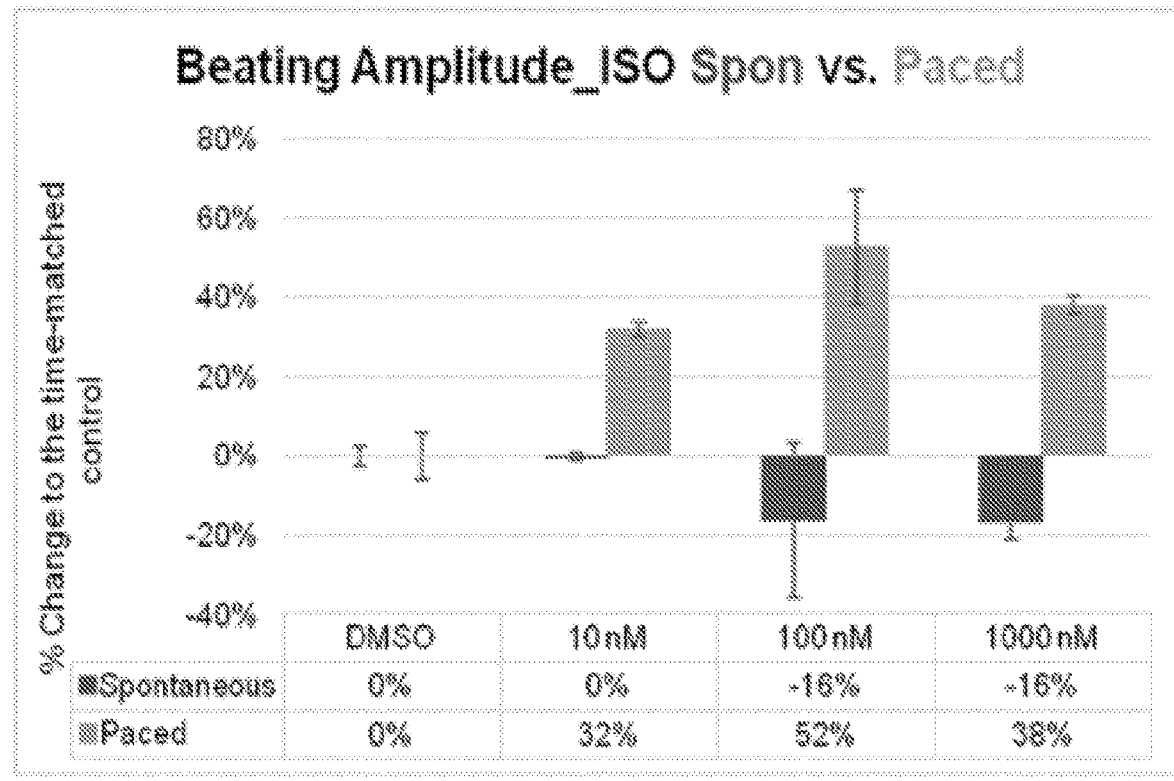
FIG. 6 is a series of graphs showing improved responsiveness of beating rate of iPSC matured cardiomyocytes compared to spontaneously beating cardiomyocytes in response to isoproterenol administration.
Figure 6B:
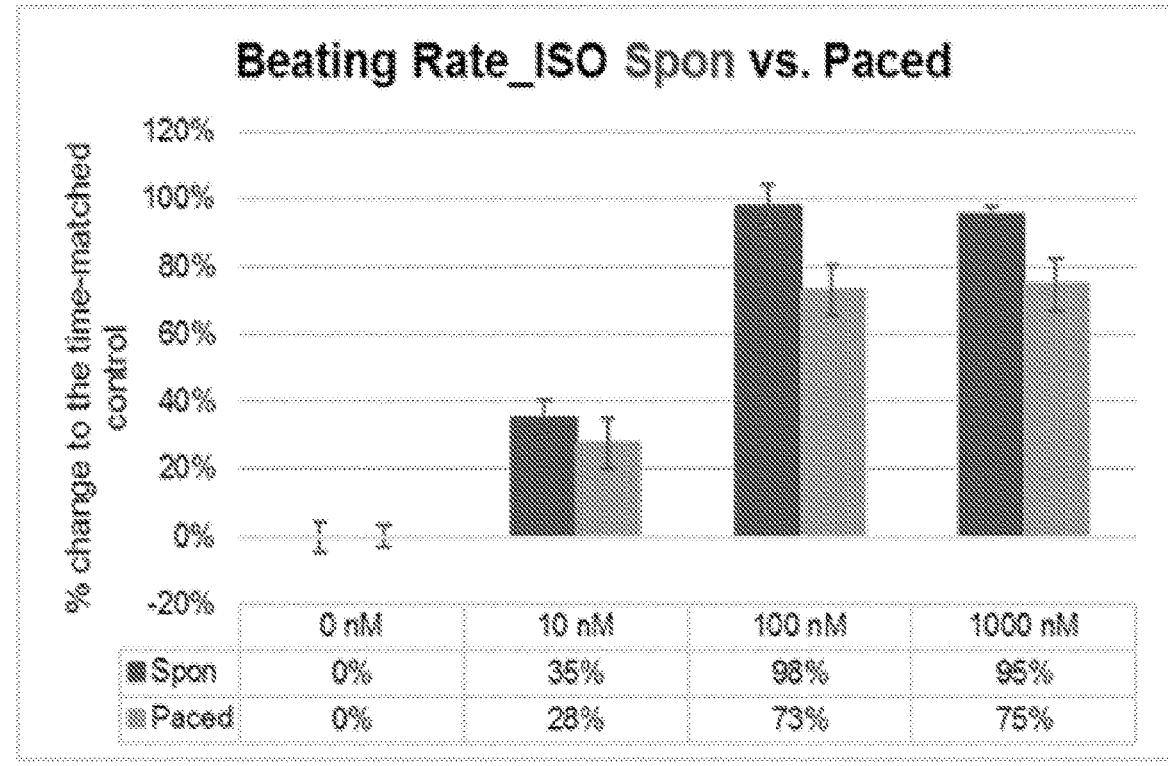

As further confirmation, Example V provides a test using inotropic compounds to determine if treated cells respond properly in the sense that positive inotropic compound treatment would result in an increase in the beating amplitude and negative inotropic compound treatment would result in a decrease in the beating amplitude. The results are depicted in FIGS. 6A-B. In summary, after exposure to isoproterenol, the increase in beating rate (B) was detected in both spontaneous beating cardiomyocytes and chronically paced cardiomyocytes, while the positive inotropic effects reflected by the increase in beating amplitude (A) was only observed in paced cells. The data was presented by mean±SD (N=5)

C. Screening for Inotropic and/or Chronotropic Compounds Using iPSC-Derived Cardiomyocytes or EC-Derived Cardiomyocytes Having a More Adult-Like Phenotype Inotropic agents, or inotropes, are medicines that change the force of heart's contractions. There are 2 kinds of inotropes; positive inotropes and negative inotropes. Positive inotropes strengthen the force of the heartbeat while negative inotropes weaken the force of the heartbeat. Both kinds of inotropes are used in the treatment of many different cardiovascular conditions. Accordingly the invention provides methods of screening for inotropes for potential therapeutic use.

The kind of inotrope given depends on the condition. Positive inotropes strengthen the heart's contractions, so it can pump more blood with fewer heartbeats. This medicine is usually given to patients with congestive heart failure or cardiomyopathy. These medicines may also be given to patients who have had a recent heart attack. In some cases, inotropes are given to patients whose hearts have been weakened after heart surgery (in cases of cardiogenic shock). Examples of positive inotropes include digoxin, amidarone, berberine, levosimendan, omecamitiv, dopamine, dobutamine, dopexamine, epinephrine, isoprenaline, antiotension.

In contrast, negative inotropes weaken the heart's contractions and slow the heart rate. These medicines are used to treat high blood pressure (hypertension), chronic heart failure, abnormal heart rhythms (arrhythmias), and chest pain (angina). They are sometimes used in heart attack patients to reduce stress on the heart and prevent future heart attacks. Examples of negative inotropes include diltiazem, verapamil, clevidipine, quinidine, procainamide, dispryramide and flecainide.

Therefore, using iPSC derived cardiomyocytes or ESC derived cardiomyocytes having a more adult-like phenotype to screen for inotropic compounds can be an important tool and provides more reproducible results compared to immature cardiomyocytes. Accordingly, the invention also provides methods of screening for potential inotropic compounds using functionally matured cardiomyocytes. Upon their identification, the compounds may be provided with a pharmaceutically acceptable carrier suitable for the intended route of administration and administered to a patient in need thereof, such as a patient suffering from congestive heart failure, cardiomyopathy, high blood pressure (hypertension), chronic heart failure, abnormal heart rhythms (arrhythmias), and/or chest pain (angina). Alternatively, the pharmaceutical may be prescribed after heart surgery.

Compounds that affect beating rate are called chronotropic compounds or chronotropes. Positive chronotropic drugs increase beating rate and include most adrenergic agonists. These include atropine, dopamine, epinephrine, isoproterenol, milrinone and theophylline. Negative chronotropic drugs decrease beating rate and include beta blockers, such as metoprolol, acetylcholine, digoxin, diltiazem and verapamil.

As demonstrated herein, the methods are able to resolve both beating force or amplitude and beating frequency at high resolution. Experimentally it is also demonstrated herein that iPSCs differentiated using the pacing approach are responsive to cardiac medications. To this end, a method of characterizing an effect of a compound on cardiomyocyte beating is provided, which includes providing a system having an electrode sensor array, wherein the system is configured to culture, electrically pulse, and electrically monitor beating cells; culturing immature cardiomyocytes in the system; electrically pacing the immature cardiomyocytes using an electric pulse profile until the cardiomyocytes are functionally mature; adding a compound suspected of having an effect on cardiomyocyte beating force or cardiomyocyte beating rate to the functionally mature cardiomyocytes; electrically monitoring the cultured cardiomyocytes before and after compound addition; determining before and after the compound addition, at least one parameter that characterizes a beating force or a beating rate; and comparing the determined at least one parameter before and after the compound addition, thereby identify a difference in response to the compound addition. From this method the compound can be characterized as a positive inotropic compound if the beating force increases after compound addition or a negative inotropic compound if the beating force decrease after compound addition, and/or a positive chronotropic compound if the beating rate increases after the compound addition or a negative chronotropic compound if the beating rate decreases after the compound addition.

Figure 7A:
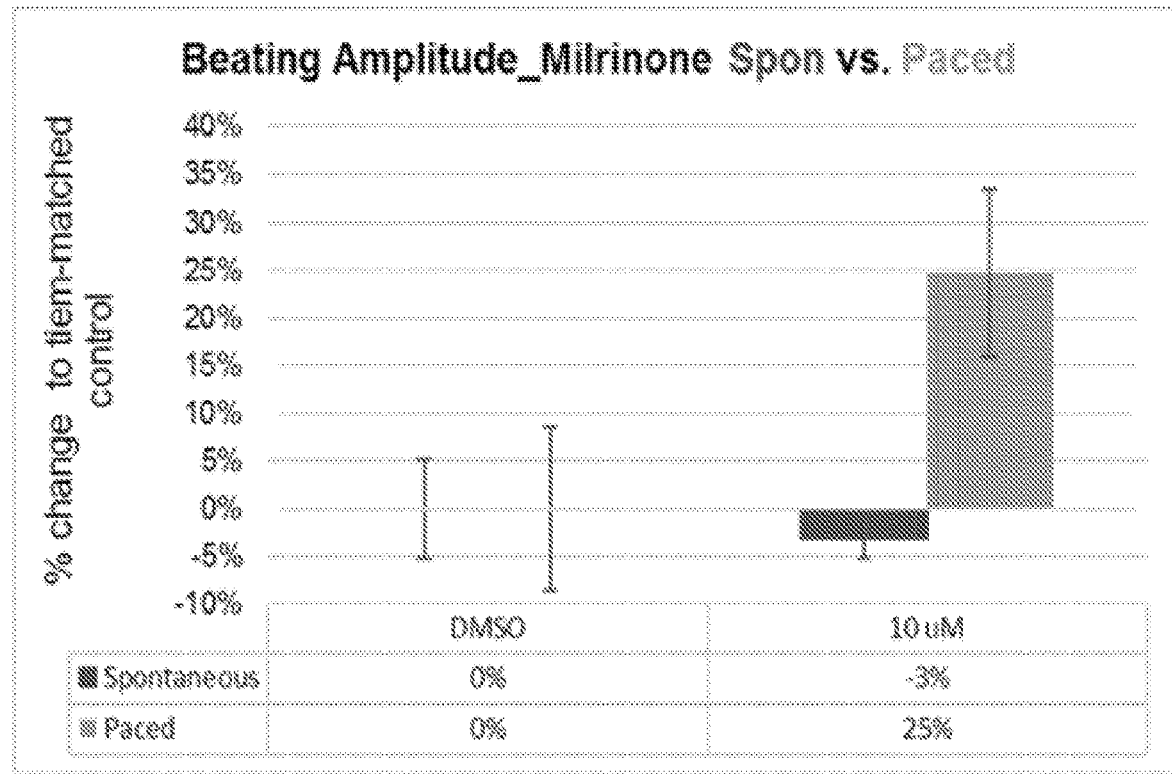
FIG. 7 is a series of graphs showing improved responsiveness of beating rate of iPSC matured cardiomyocytes compared to spontaneously beating cardiomyocytes in response to milrinone administration.
Figure 7B:
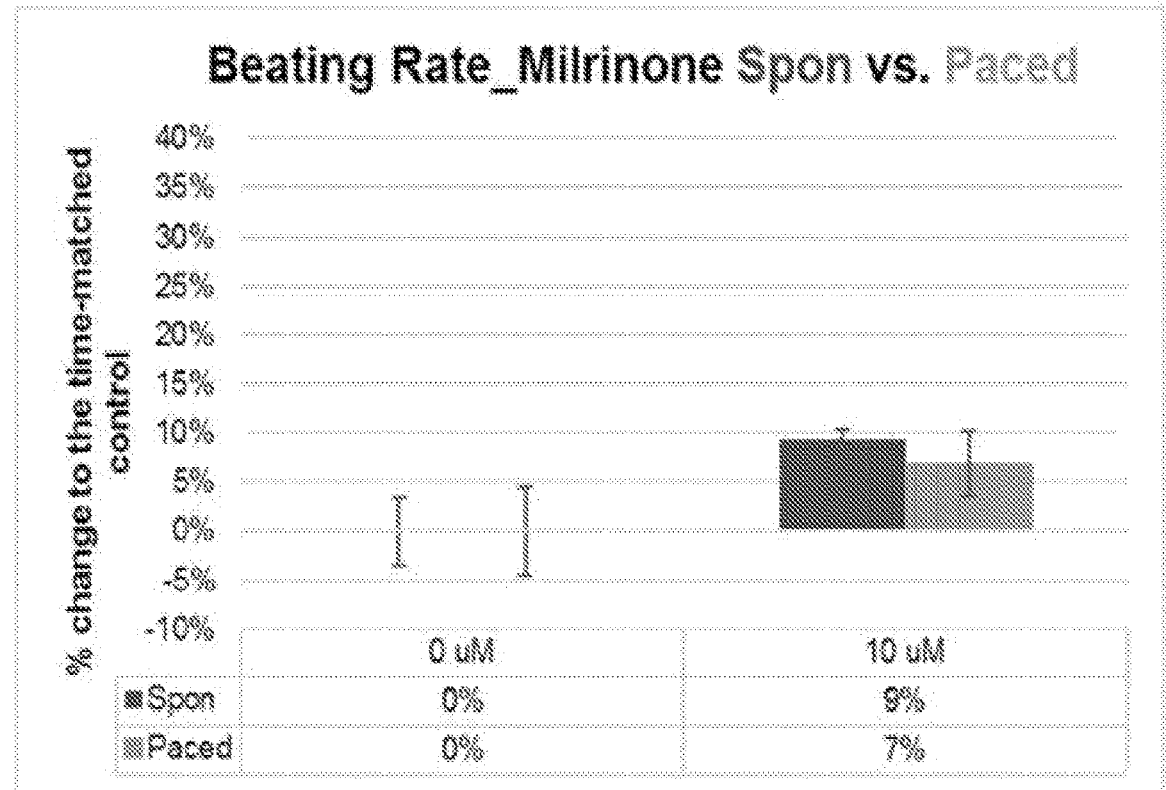

As proof of principle, an assay was conducted in Example VI using milrinone. As shown in FIG. 7A-B, after exposure to the positive inotropic compound milrinone, beating rate (B) slightly increased in both spontaneous beating cardiomyocytes and chronically paced cardiomyocytes. However, the beating amplitude (A) was significantly increased in electrically paced cardiomyocytes. The data was presented by mean±SD (N=5).

Further analysis was conducted to assess whether the beating force would increase upon administration of a panel of additional inotropic compounds. FIG. 8 displays a panel of force frequency displays after administration of a panel of inotropic compounds before and after electrically pacing iPSC cardiomyocytes. Positive intropic compounds bayK and digoxin where shown to have a positive inotropic effect, while ISO has positive chronotropic effect.

As with the systems described above and with brief reference to FIGS. 1-2D, the electrode array 10A-D can include an impedance monitoring electrode array 16A-D, 18A-D positioned on a substrate and operably connected to an impedance analyzer 110B to monitor cell-substrate impedance of a cell population cultured in the system 100. Alternatively, the electrode array 10A-D can include an extracellular recording electrode array 12A-D, 14A-D operably connected to an extracellular recording amplifier 110C to conduct extracellular recording of a cell population cultured in the system 100. Still further, the system 100 can include an impedance monitoring electrode array 16A-D, 18A-D on a substrate, an extracellular recording electrode array 12A-D, 14A-D on the substrate, an impedance analyzer 110B, and an extracellular recording amplifier 110C, where the system 100 is configured to monitor cell-substrate impedance and conduct extracellular recording of a cell population cultured in the system 100.

As a nonlimiting example, the methods can be conducted using the xCELLigence RTCA CardioECR system (shown in FIG. 1), by: seeding iPSC cardiomyocytes in wells of the CardioECR Plate (E-Plate CardioECR 48) at an appropriate density; allowing the cells to attach, grow and achieve spontaneous beating rhythm while continuously monitoring the spontaneous beating activity using the CardioECR system; and performing directed electrical pacing of the iPSC cardiomyocytes after spontaneous, synchronously beating is observed for the cardiomyocyte monolayer, over the course of 4 weeks post-seeding while continually monitoring beating activity.

A compound suspected of having an effect on cardiomyocyte beating force or cardiomyocyte beating rate to the functionally mature cardiomyocytes can be added directly to the device and the cardiomyocytes electrically monitored over time. Preferably, the cardiomyocytes are electrically monitored before and after compound addition. In some embodiments, the cardiomyocytes are compared to a control population that does not receive a compound. At least one parameter that characterizes a beating force or a beating rate is then determined and compared to identify whether addition of the compound affected the beating parameter.

For completeness, the method is not limited to any particular species, but the methods will most often use a cell from a same species that is to ultimately be diagnosed or treated with the compound. To this end, when conducting assays that may lead to the treatment of a human, such as for the treatment of a heart disorder, most often human iPSCs will be used. When conducting studies for veterinary medicine, most often iPSCs or ESCs from a same species that is to be diagnosed or treated will be used. Still further, when the object is to diagnose or treat a human patient, most preferably the iPSCs will be from cells collected from the same patient that is to be treated or diagnosed.

While the methods provide for the further differentiation of immature cardiomyocytes, the initial differentiation procedures can also be conducted on the cell cultured device and electrically monitored. More specifically, coatings used in the differentiation of iPSCs into cardiomyocytes may also be applied to the cell culture device and corresponding procedures performed.

In some embodiments, the assay is performed with the immature cardiomyocytes aligned on patterned substrates. As a nonlimiting example, culturing cardiomyocytes on patterned islands of fibronectin separated by bare polyacrylamide, which is cytophobic, was shown to improve spontaneous beating. Werley et al. (2017). As such, the methods herein may include culturing immature cardiomyocytes on patterned substrates, such as, but not limited to fibronectin patterns as taught or suggested in Werley et al, with the addition of the electrodes for pulsing and electrically monitoring cardiomyocytes. That is, the devices for iPSC maturation can be patterned to further drive maturation.

In some embodiments, the assay is performed on a substrate having an elastic modulus from 1 kPa to 50 kPa, 5 kPa to 15 kPa, 8 kPa to 12 kPa, or 10 kPa, which is near the stiffness of the native myocardium. Such substrates can be formed following the teachings of Jacot et al (2008) with the addition of electrodes for pulsing and electrically monitoring cardiomyocytes. That is, the devices for iPSC maturation have an elastic modulus that mimics the myocardium.

In some embodiments, the assay is performed in the presence of a vascular-like network. As a nonlimiting example, the immature cardiomyocytes are seeded on a vascular network of endothelial cells (ECs). Vascular ECs produce a variety of auto- and paracrine agents including VEGF, angiopoietin and nitric oxide that influence cardiomyocyte metabolism, growth, contractility, and rhythmicity of the heart. Brustaert (2003). In other embodiments, the immature cardiomyocytes are seeded on a vascular network of fibroblasts. In other embodiments, the immature cardiomyocytes are seeded on a vascular network of human umbilical vein endothelial cells (HUVEC) and human adipose stromal cells (hASC). Adipose stromal cells (hASCs) have been shown to produce significant amounts of angiogeneic factors and cytokines including VEGF, hepatocyte growth factors and angiopoietin. In other embodiments, the immature cardiomyocytes are seeded on a vascular network of HUVECs and human foreskin fibroblasts. Each of the above have been shown to be beneficial for culturing cardiomyocytes. Vourenpaa et al. (2004). Each can be used with the methods and systems herein.

Preferably, the pacing is conducted on a cardiomyocyte population that is undergoing synchronized beating. Synchronized beating can be determined using cell-substrate impedance monitoring of the immature cardiomyocytes to obtain a beating parameter, whether raw impedance value or cell index, then comparing the parameter over time. A population that is not synchronized in beating will not generate a continuous and reproducible impedance-based curve. Nor will the beating culture produce a reproducible beating peak. That is, the curves will not properly overlay one another. Rather the curve will shift or lack refinement. To this end, cardiomyocyte beating resolution as provided herein is sufficiently high that it can determine whether or not the cardiomyocyte beating is synchronized. The systems herein regularly achieve 40 ms resolution and also reproducibly achieve 20 ms resolution. By 40 ms resolution or 20 ms resolution it is meant that the system will conduct consecutive measurements 40 ms or 20 ms apart from one another. Still greater resolution of 10 ms or 1 ms is also encompassed. Typically, cell populations are measured over time periods of about 20 seconds and during this time preferably the pacing is halted. Achieving synchronized beating without electric stimulation will generally occur in 6 days to 2 weeks.

It has been found that synchronized beating can be achieved faster by electrically pacing the immature cardiomyocytes. That is, if the cardiomyocyte beating is not synchronized, the method can also include electrically pacing the immature cardiomyocytes until cardiomyocyte beating is synchronized. Compared to the pulse profiles used for differentiation, electrically pacing the cardiomyocytes to synchronize beating typically maintains a slower pulse frequency. That is, immature cardiomyocytes can be slowly but steadily paced until beating is synchronized. Typically, the pacing is at a constant frequency. Most preferably, the pacing is at the same pace as the beating rate of the immature cardiomyocytes in culture. This frequency is typically about 0.5 Hz to about 1 Hz. This frequency could be 0.05 Hz to 0.5 Hz in some cases (e.g. diseased genotype/phenotype). Pacing to achieve synchronized beating typically occurs within days.

Pacing the immature cardiomyocytes includes electrically delivering a pulse profile to the immature cardiomyocytes that induces further differentiation. Most preferably, the pulse profile has a rectangular pulse shape and an intensity of about 0.7 V to 1 V or up to 2 volts. In some embodiments the voltage is up to 3 volts. However, other pulse shapes such as a sine wave form, a triangle wave form and/or a sawtooth wave form can also be used. In some instances intensity is increased when pacing frequency is increased, but in others intensity remains uniform. The pulse duration is generally about 0.1 millisecond to 0.2 milliseconds or up to 10 milliseconds and can also increase when pacing frequency is increased. However, pulse duration can also be maintained uniform while increasing pulse frequency over time.

While the pulse intensity and duration can be increased over time, accelerating the differentiation of immature cardiomyocytes is believed to be primarily due to increasing the beating rate of the cell culture, which is by way of electric pacing of cells. Experimentally it was found that increasing the beating rate over time increases the rate of differentiation. To this end, what could take months to a year or so to accomplish is demonstrated herein to take place within weeks. Surprisingly beneficial results were achieved when holding a pacing frequency at a same rate for 1 one week, then increasing the pacing by about 0.5 Hz weekly until achieving a pacing frequency of 2 Hz. However, it is expected that shorter periods, such as days, would be acceptable as would longer durations, such as weeks.

Accordingly, a pulse profile to induce differentiation of immature cardiomyocytes into those with an adult phenotype can include electrically pacing cardiomyocytes by applying a pulse profile having a pulse frequency between 1 Hz and 2 Hz. Most preferably the pulse profile increases the pulse frequency over time. In embodiments, where the immature cardiomyocytes are beating at a frequency of less than 1 Hz, the pulse frequency applied may double in frequency over time. Electric pacing continues until the cardiomyocytes have a positive force-frequency relationship. In particular, functionally mature or adult cardiomyocytes have a positive force-frequency relationship; whereas immature cardiomyocytes have a negative force frequency relationship.

As with monitoring the functional maturation of cardiomyocytes, the high resolution of cardiomyocyte beating reveals shifts in beating force and/or frequency when adding compounds that correspondingly affect beating force and/or frequency. That is while the methods use electric monitoring of cardiomyocytes to follow the differentiation into mature cardiomyocytes, the same electric monitoring approach can measure and follow the effect of potentially therapeutic or toxic compounds on cardiomyocytes. In particular, the electric monitoring of cardiomyocytes can reveal changes in beating force or amplitude and can be reveal changes in beating frequency in response to compound addition.

Thus, by monitoring the beating force or amplitude and beating frequency both inotropic and chronotropic affects can be evaluated. As a nonlimiting example, comparing the determined at least one parameter before and after the compound addition can be used to characterize the compound as: a positive inotropic compound if the beating force increases after compound addition or a negative inotropic compound if the beating force decrease after compound addition, and/or a positive chronotropic compound if the beating rate increases after the compound addition or a negative chronotropic compound if the beating rate decreases after the compound addition.

D. Screening for Compounds Using iPSC-Derived Cardiomyocytes or ESC-Derived Cardiomyocytes that Affect the Maturation of Cardiomyocytes into a More Adult-Like Phenotype The artisan will appreciate that the methods can also be applied to assess the effect of compounds on the maturation process. As an exemplary embodiment, a method of characterizing an effect of a compound on cardiomyocyte maturation is provided, the method including: providing a system configured to culture, electrically pace, and monitor beating of beating cells; culturing immature cardiomyocytes in the system; electrically pacing the immature cardiomyocytes according to a pulse profile that functionally matures the cardiomyocytes; adding a compound suspected of having an effect on cardiomyocyte maturation; electrically monitoring the cultured cardiomyocytes before and after compound addition; determining before and after the compound addition, at least one parameter that characterizes a beating force-frequency relationship; comparing the determined at least one parameter before and after the compound addition thereby identify a difference in response to the compound addition.

Relatedly, a method of characterizing an effect of a compound on cardiomyocyte beating is provided, which includes: providing a system configured to culture, electrically pace, and monitor beating of beating cells; culturing two populations of immature cardiomyocytes in the system; adding a compound suspected of having an effect on cardiomyocyte maturation to one of the populations of immature cardiomyocytes; electrically pacing the two populations of immature cardiomyocytes according to a pulse profile that functionally matures immature cardiomyocytes until at least one of the two populations of cardiomyocytes is functionally mature; and characterizing the compound as further driving maturation if the population with compound addition functionally matures before the other cardiomyocyte population.

As with the disclosure above, in some embodiments, the immature cardiomyocytes are derived from induced pluripotent stem cells (iPSCs) or embryonic stem cells (ESCs). It is preferred that both populations of immature cardiomyocytes are cultured until beating within the corresponding population is synchronized prior to adding the compound. That is, each population of cardiomyocytes should have synchronized beating but the beating between the two different populations does not need to be synchronized. Synchronized beating can be determined using cell-substrate impedance monitoring of the immature cardiomyocytes to obtain a beating parameter, whether raw impedance value or cell index, then comparing the parameter over time. A population that is not synchronized in beating will not generate a continuous and reproducible impedance-based curve. Nor will the beating culture produce a reproducible beating peak. That is, the curves will not properly overlay one another. Rather the curve will shift or lack refinement. To this end, cardiomyocyte beating resolution as provided herein is sufficiently high that it can determine whether or not the cardiomyocyte beating is synchronized. The systems herein regularly achieve 40 ms resolution and also reproducibly achieve 20 ms resolution. By 40 ms resolution or 20 ms resolution it is meant that the system will conduct consecutive measurements 40 ms or 20 ms apart from one another. Still greater resolution of 10 ms or 1 ms is also encompassed. Typically, cell populations are measured over time periods of about 20 seconds and during this time preferably the pacing is halted. Achieving synchronized beating without electric stimulation will generally occur in 6 days to 2 weeks.

Pacing the immature cardiomyocytes includes electrically delivering a pulse profile to the immature cardiomyocytes that induces further differentiation. Most preferably, the pulse profile has a rectangular pulse shape and an intensity of about 0.7 V to 1 V or up to 2 volts. In some embodiments the voltage is up to 3 volts. However, other pulse shapes such as a sine wave form, a triangle wave form and/or a sawtooth wave form can also be used. In some instances intensity is increased when pacing frequency is increased, but in others intensity remains uniform. The pulse duration is generally about 0.1 millisecond to 0.2 milliseconds or up to 10 milliseconds and can also increase when pacing frequency is increased. However, pulse duration can also be maintained uniform while increasing pulse frequency over time.

While the pulse intensity and duration can be increased over time, accelerating the differentiation of immature cardiomyocytes is believed to be primarily due to maintaining an increasing beating rate of the cell culture, which is by way of electric pacing of cells. Experimentally it was found that increasing the beating rate over time increases the rate of differentiation. To this end, what could take months to a year or so to accomplish is demonstrated herein to take place within weeks. Surprisingly beneficial results were achieved when holding a pacing frequency at a same rate for 1 one week, then increasing the pacing by about 0.5 Hz weekly until achieving a pacing frequency of 2 Hz. However, it is expected that shorter periods, such as days, would be acceptable as would longer durations, such as weeks.

Accordingly, a pulse profile to induce differentiation of immature cardiomyocytes into those with an adult phenotype can include electrically pacing cardiomyocytes by applying a pulse profile having a pulse frequency between 1 Hz and 2 Hz. Most preferably the pulse profile increases the pulse frequency over time. In embodiments where the immature cardiomyocytes are beating at a frequency of less than 1 Hz, the pulse frequency applied may double in frequency over time. Electric pacing continues until the cardiomyocytes beat at a positive force-frequency relationship. In particular, the functionally adult cardiomyocytes have a positive force-frequency relationship; whereas immature cardiomyocytes have a negative force-frequency relationship.

During or before electrical pacing, one or more compounds can be added to an immature cardiomyocyte population and its effect on maturation assessed by way of comparison to a control. That is, the force-frequency relationship between cell populations in response to compound addition can be compared to determine whether the added compound further drives maturation or slows maturation. The skilled artisan will appreciate that determining changes in maturation in response to compound administration may be further studied by providing such compounds in different concentrations to determine dose effects on maturation.

As with monitoring maturation, compounds may be administered to one or more populations of immature cardiomyocytes and the force-frequency relationship assessed over time. Changes in force-frequency relationship in response to compound administration demonstrates differences in maturity or the maturation process.

EXAMPLES

Example I

Determining Beating Parameters of a Beating Cell Culture

In one approach cell-substrate impedance measurements are used to determine beating cycle peaks associated with a cell. Beating itself corresponds to the excitation-contraction coupling of the cells. In particular, beatings are defined as a sequence of Positive Peaks (+P in FIG. 3) and Negative Peaks (−P in FIG. 3). The value of these Positive Peaks and Negative Peaks and the corresponding time periods determine beating characteristics, which reveal the status of the cardiomyocyte population. For example, a Positive Peak may correspond to the contraction of cardiomyocytes, whilst the return of measurement values to baseline and to negative peak may correspond to the relaxation of cardiomyocytes.

As an example, time dependent impedance values or cell index values for a well are analyzed by deriving their first order derivatives and second order derivatives using numerical methods. The beating cycle peaks are those data points where the first order derivatives of impedance values or cell index values are zero or close to zero in absolute value. If the beating cycle peak is a positive peak (i.e. peak corresponds to a maximum value in measured impedance or cell index over the beating cycle), then the peak would correspond to data points where the second order derivatives of the impedance values or cell index values are negative and where the first order derivatives of the impedance values or cell index values are zero or close to zero in absolute value. If the beating cycle peak is a negative peak (i.e. peak corresponds to a minimum value in measured impedance or cell index over the beating cycle), then the peak would correspond to the data points where the second order derivatives of the impedance values or cell index values are positive and where the first order derivatives of the impedance values or cell index values are zero or close to zero in absolute value.

In yet another approach, the method for searching for and identifying "positive peaks" and "negative peaks" may involve the use and modification of various mathematical algorithms, e.g., the Douglas-Peucker algorithm. The Douglas-Peucker algorithm is an algorithm for reducing the number of points in a curve that is approximated by a series of points. Based on the required maximum distance between on the original curves and on the simplified curves, the Douglas-Peucker algorithm could also be adopted to identify positive peaks and negative peaks in time-dependent data point series for impedance values and/or cell index vales.

In another approach, a method of determining a beating cycle peak is to search for the data point where the trend of the data changes direction from "increasing" to "decreasing" with time (for a positive peak), or from "decreasing" to "increasing" (for a negative peak). After the identification of the beating cycle peaks, the impedance or cell index values at such peak time points provide the magnitude or amplitude of the beating cycle peaks.

After determining the beating cycle peaks, various methods can be used to calculate the beating rate. A beating rate parameter is generally provided as beatings per minute. In a positive peak counting approach, the number of positive peaks is determined over a given time interval and converted to the desired unit, preferably beats per minute. Similarly, in a negative peak counting approach the number of negative peaks is determined over given time interval and converted to the desired unit. As an example, if there are 2 peaks in a one second interval, then the beating rate would be 2 beats per second, or 120 beats per minute. In still another approach, beating rate is calculated by determining the time period between a series of two or more positive peaks or between a series of two or more negative peaks. That is, in this approach a unit of time (e.g., 1 minute) is divided by the time period between two adjacent peaks. For example, if two adjacent peaks are separated by 500 milliseconds, then the beating rate would be 120 beats per minute. In a time interval comprising multiple positive or negative peaks, the beating rate could be determined by the following method. Take positive peaks as an example, the time periods between every pairs of two adjacent positive peaks are calculated. Then the beating rate could be calculated in two ways. The first method is to divide a unit of time (e.g., 1 minute) by the average of the time periods between all two-adjacent positive peaks in the given time interval. The second method is to calculate the corresponding beating rates based on each pair of two adjacent positive peaks and then to average of the adjacent-peaks-derived beating rates.

To further assist in comparison, beating rates can also be normalized. Determining a normalized beating rate is achieved by dividing the beating rate at a selected data analysis time by a beating rate at a normalization time. Thus a beating rate identical to that at the normalization time would be defined as 1. Normalizing beating rates can provide a more clear indication of whether and to what degree a change in beating rate occurs. For example, a normalized beating rate close to 1 or less than 1 could mean that further maturation has not occurred, which suggests a pulse profile should be continued to further induce maturation. A normalized beating rate larger than 1 may mean that the iPSC has undergone maturation or is still undergoing maturation.

Beating amplitude or beating force is a parameter used in some embodiments to describe or correspond to the intensity of the peak, which may reflect the extent of contraction or relaxation of cardiomyocytes during a beating cycle. Determining beating amplitude can involve a whole peak approach, which could be determined by the difference between a negative peak and the following positive peak as shown in FIG. 3. For example, in FIG. 3 the beating amplitude is shown as the difference in cell index between a Negative Peak to the following adjacent Positive Peak (Amp-1, Amp-2, Amp-3, . . . , Amp-m). In another approach, beating amplitude for a positive peak is the difference between a determined baseline to a positive peak. In still another approach beating amplitude for a negative peak is the difference between a determined baseline to a negative peak. An exemplary baseline is shown in FIG. 3.

Thus, for a single beating cycle, one could define or identify different types of amplitude (or an amplitude) of the beating-cycle peaks, including the amplitude of positive peak, the amplitude of negative peak and the amplitude of the whole peak in a cycle. From the measured data point series, a baseline value, which may theoretically correspond to the value when the cardiomyocytes are at their fully relaxation status, could be determined or identified from the measured data values in a time series. The amplitude of a positive peak is the impedance value or cell index value or other measurement value at the positive-peak time point subtracted by the baseline value. The amplitude of a negative peak is the impedance value or cell index value or other measurement value at the negative-peak time point subtracted by the baseline value. The amplitude of whole peak is the difference in the impedance value or cell index value or other measurement value between positive-peak time point and negative-peak time point.

Whilst the above paragraph discusses different types of the amplitudes of a single beating cycle, for a time period including multiple beating cycles, one could determine the average and standard deviations (or standard errors) of the positive-peak amplitude, the negative-peak amplitude and whole-peak amplitude.

Beating amplitude can also be normalized as a normalized amplitude. A normalized amplitude is the amplitude at a selected data analysis time divided by the amplitude at the normalization time point. A beating amplitude identical to that at the normalization time would be defined as 1. Thus, the normalized amplitude reveals differences, such as an increase or decrease in the amplitude or intensity of a beat compared to a referenced amplitude, where generally an increase is indicative of further maturation.

Normalized beating amplitude could be derived for all three types of beating amplitudes, i.e. positive-peak based amplitude, negative-peak based amplitude and whole-peak amplitude.

Beating period (also referred to as "beating cycle") is a parameter which provides the time period between two positive peaks, two negative peaks or can be the time period between a positive peak and a negative peak. The beating period can be used to identify changes in beating rate or can be used as a defined period for comparison of other parameters, such as differences in amplitude. In FIG. 3, within one Sweep Duration, the number of Positive Peaks is m (+P1, +P2, +P3, . . . , +Pm) and the number of Negative Peaks is n (−P1, −P2, −P3, . . . , −Pn). The time between two adjacent individual Positive Peaks (or/and two adjacent individual Negative Peaks) is defined as beating period. For example, the beating period based on the Positive Peaks is $T_{+P1}$, $T_{+P2}$, . . . , $T_{+P(m-1)}$ and the beating period based on the Negative Peaks is $T_{-P1}$, $T_{-P2}$, . . . , $T_{-P(n-1)}$.

Example II

Comparing Beating Patterns

Beating pattern similarity is a parameter derived to quantify the degree of the similarity between the beating waveforms between two different time intervals. To this end, the beating pattern similarity can be used to determine whether cardiomyocyte beating is synchronized or if affected by inotropic or chronotropic compound administration. For any given time interval, the beating pattern is shown as the beating curves comprised of a number of measurement values (impedance values, cell index values or other values) across a number of time points during the time interval. Beating patterns at two time intervals may be compared numerically, such as by comparison between determined parameters for the beating curves at these two time intervals or patterns may be compared through the comparison of the beating curves. When comparing curves it may desirable to align curves to match an initial positive peak or initial negative peak. Aligning curves may also use a variety of curve algorithms, which identify distances or shifts between curves.

In one embodiment, the beating pattern similarity is derived as a parameter to compare the determined parameters for the beating curves at two time intervals. For example, one may compare the beating rates $BR_1$ and $BR_2$ at the two time intervals. An example of the beating pattern similarity is given as:

Beating pattern similarity=$(2*BR_1*BR_2)/(BR_1*BR_1+BR_2*BR_2)$

With this above example, the beating pattern similarity is one (the highest value) when the beating rates at the two time intervals are the same. When the beatings rates differ at two time intervals, the beating pattern similarity would be less than 1. The more the beating rates differ, the smaller the beating pattern similarity value.

In a preferred embodiment, however, the beating pattern similarity is derived as a parameter to directly compare the beating curves at the two time intervals. The idea of the beating pattern similarity should possess such properties that the value for beating pattern similarity is large when the two beating curves are similar, and the value for beating pattern similarity is small when the two beating curves are not similar. There are multiple methods for deriving such beating pattern similarity values.

In one method, as briefly mentioned above, for comparing the beating curves at two time intervals (assuming the same measurement time resolutions for the measured data points), it may desirable to align curves to match an initial positive peak or initial negative peak. After aligning the initial peaks, an "AND" operation is performed on the time points for the two beating curves so that the overlapping time points on the two beating curves are kept whilst non-overlapping time points on either one of the beating curves are discarded. Thus, the remaining, overlapping data points on the two beating curves are of the same number and it is possible to readily define a distance to describe whether the two beating curves are similar. For example, the beating pattern similarity could be the correlation coefficient between the two data series in the remaining portions of the two beating curves. Clearly, the more similar the two curves, the larger the correlation coefficient (i.e., the larger the beating pattern similarity value is). In another example, the beating pattern similarity could simply be certain mathematically-defined-distance (e.g. Euclidean distance) between two data series in the remaining portion of the two beating curves. Note that if the measurement time resolutions differ between the measured data points, additional time points may be artificially inserted into the beating curves with missing time points after mathematically interpolation of the values for such added time points based on other measured data points. With this operation, the two beating curves would have the same time resolutions.

In another method for comparing the beating curves at two time intervals (again, assuming the same measurement time resolutions for the measured data points), one would take the beating curve (out of the two) with the shorter time duration. If the time-shorter beating curve comprises more than half of the data points of the other beating curve, then some last data points from the shorter beating curve are removed to form a "base-curve" so that the number of the remaining data points in the shorter beating curve is half of the number of the data points in the other beating curve. Then a number of correlation coefficients would be determined where each correlation coefficient corresponds to the base-curve aligned to one continuous segment (comprising of the same data point number as the base-curve) of the other beating curve. For example, the first correlation coefficient is determined between the data series of the base curve and the data series of first half of the other beating curve (starting from the first data point). The second correlation coefficient is determined between the data series of the base curve and the data series from the other beating curve with starting point being the second data point. The last correlation coefficient is determined between the data series of the base curve and the data series from the second half of the other beating curve ending with the last data point. Finally, the beating pattern similarity is determined as the maximum value of all the correlation coefficients.

There may be other methods or algorithms that could be used for deriving beating pattern similarities. Beating pattern similarity could be used to analyze the effect of a compound on the beating pattern of cardiomyocytes. The beating curves from two time intervals are compared. For analyzing the effect of a compound, one time interval corresponds to the time period before compound treatment whilst the other time interval corresponds to the time period after compound treatment. The beating pattern similarity has an advantage over other parameters in comparing compound's effect on the cardiomyocytes. The advantage is that it could include or summarize all the effects due to the compound, i.e. the effects on the beating rates, beating waveform shapes or beating amplitudes etc could all be included into the single parameter of the beating pattern similarity.

Beating rhythm irregularity (BRI) is a parameter which identifies changes in beating rate or changes between peak periods for a beating curve over a time interval. Beating rhythm irregularity is also referred to as a beating rate irregularity index. If the beating rate or the beating peak period does not change with time, then the beating rhythm is regular and the parameter of the beating-rhythm-irregularity should be small, i.e. being zero or close to zero. On the other hand, if the beating rate or beating period does change with time, then beating rhythm is irregular and the parameter of the beating rhythm irregularity should have a large value. As one requirement, the parameter of the beating rhythm irregularity should be able to identify the arrhythmic beating of cardiomyocytes. Thus, the beating-rhythm-irregularity should attain a large value for the beating curves of cardiomyocytes if the cardiomyocytes exhibit arrhythmic beating. There are multiple methods for calculating the beating rhythm irregularity for a beating curve over a time interval. For example, the positive peak periods for each-adjacent-positive-peak-pair are calculated for the beating curve in the given time interval. Then the average and standard deviation of such multiple positive peak periods are calculated. The beating rhythm irregularity can be calculated by dividing the standard deviation of the positive peak periods by the average. In another example, the negative peak periods for each adjacent negative peak pair are calculated for the beating curve in the given time interval. Then the average and standard deviation of such multiple negative peak periods are calculated. The beating rhythm irregularity can be calculated by dividing the standard deviation of the negative peak periods by the average.

Example III

Functionally Maturing iPSC Cardiomyocytes by Directed Electrical Pacing Using the CardioECR System The iPSC derived cardiomyocytes used here are iCell Cardiomyocytes[2] (iCell CM[2]), which were purchased from Cellular Dynamic Internationals (CDI). iCell CM[2] were thawed and seeded in fibronectin pre-coated E-plate CardioECR 48 at 50,000 viable cells/well according to CDI user's guide. The attachment, growth and beating activity of the cells were recorded in real-time using xCELLigence RTCA CardioECR station, which is permanently placed in the 37° C. tissue culture incubator.

Electrical pacing was initiated and applied to the cell monolayer after a stable and robust beating activity of iCell CM[2] was observed using xCELLigence RTCA cardioECR system, which generally appears between 6-8 days after plating cells in the E-plate CardioECR 48. The cells were continuously paced at 1 Hz, 1.5 Hz and 2 Hz with optimal pulse setting at each pacing frequency for 1 week respectively in the CardioECR station. Medium change was performed daily. Thus, the cells were continuously paced for 3 weeks (week 1: 1 Hz pacing; week 2: 1.5 Hz pacing; week 3: 2 Hz pacing). We found that such a pacing schedule with gradually-increased pacing frequencies is quite effective in achieving cardiomyocyte maturation through such frequency ramping up electrical pacing. FIG. 4 shows a screenshot of beating activity recorded continuously over 6 seconds for each stage of pacing.

Example IV

Assessing the Functional Maturation of Electrostimulated iPSC Cardiomyocytes

To assess the functional maturation of iPSC cardiomyocytes using electrical pacing we conducted the following procedure. After completion of the maturation process using the ramping up electrical pacing approach in Example III, the pacing was paused for 6 hours prior to the test for force-frequency relationship to ensure that cells stabilized their beating activity, in terms of beating rate and beating amplitude. The baseline of beating activity was recorded for 20 seconds every 5 minutes up to 30 minutes immediately prior to the test. The beating rate of cells was then gradually increased by continuously electrical pacing at 0.75 Hz, 1 Hz, 1.5 Hz and 2 Hz for 10 min respectively. The contractile activity of cells was recorded for 20 seconds at the end of each pacing at different frequencies. The surrogate of contractile force, beating amplitude, obtained at each beating frequency was calculated using CardioECR data analysis software and plotted over beating frequencies.

FIG. 5 depicts the results of an exemplary study, where a positive beating amplitude and beating frequency relationship was observed in paced cardiomyocytes, which is indicate of a mature phenotype. Briefly, the cells were first electrically paced at 1 Hz, 1.5 Hz and 2 Hz for 1 week respectively (week 1, 1 Hz pacing, week 2 1.5 Hz pacing and week 3, 2 Hz pacing). The electrical stimulation at 2 Hz was terminated 5 hours prior to the test of beating amplitude and beating frequency relationship. The beating amplitude was calculated at each beating frequency which was controlled by the electrical stimulation. The data collected from non-paced cardiomyocyte (spontaneous beating cardiomyocytes) was presented in blue. The data collected from chronically paced cardiomyocytes was presented in orange.

Example V

Assessing Functional Maturation of Electrostimulated iPSC Cardiomyoctyes Using Inotropic Compounds The functional maturation of iPSC cardiomyocytes from Example III was tested using inotropic compounds. Results are shown in FIG. 6A-B.

In particular, iPSC cardiomyocytes were seeded in the wells of the CardioECR Plate (E-Plate CardioECR 48) for approximately 7 days until they formed a synchronous, stable beating monolayer. The cells were then electrically paced at 1 Hz, 1.5 Hz and 2 Hz for 1 week respectively (week 1: 1 Hz pacing; week 2: 1.5 Hz pacing; week 3: 2 Hz pacing). After pausing the 2 Hz pacing, cell media was replaced with 90 µL of fresh pre-warmed media the night before compound addition.

The cells were then continuously paced for additional 8 hours at 2 Hz. The electrical pacing was terminated 5 hours prior to compound addition to ensure that cells would generate a stable beating rate and beating amplitude for treatment. The baseline beating activity was recorded for 20 seconds every 5 minutes up to 30 minutes immediately prior to compound addition. 10 µL of 10× compound solution was then added to the wells of CardioECR plate using a multichannel pipette. The cell response to the compound was recorded for 20 seconds every 2 minutes immediately after compound exposure using CardioECR system. The cell beating activity, including beating rate and beating amplitude, was evaluated at 30 minutes post compound addition.

Example VI

Screening for Potential Inotropic Compounds Using Functionally Mature Cardiomyocytes To demonstrate the use of functionally matured iPSCs to identify inotropic compounds, electrostimulated iPSCs were tested for their response to administration of the compound milrinone.

Cell monolayer preparation. The iPSC-derived cardiomyocytes were seeded at the optimal seeding density in the wells of E-plate CardioECR 48, which were pre-coated with substrate. The attachment, growth and beating activity of the cells were recorded after cell seeding in real-time using xCELLigence RTCA CardioECR station, which was placed in a 37° C. tissue culture incubator. Medium change was performed every other day.

Induction of functionally mature iPSC-derived cardiomyocytes. The electrical pacing was initiated and applied to the cell monolayer after a stable and robust beating activity of iPSC-derived cardiomyocytes is observed using xCELLigence RTCA cardioECR system. The iPSC-derived cardiomyocytes were then electrically paced at 1 Hz, 1.5 Hz and 2 Hz for 1 week respectively using xCELLigence RTCA CardioECR system. The pulse intensity and pulse duration was optimized before each pacing frequency and continuously applied to the cells. The cells were confirmed to beat at the same frequency as the pacing frequency under the pacing condition. Medium change was performed every day during chronic pacing procedure.

Inotropic compound screening. After completion of functional maturation of cardiomyocytes over the course of ramping up pacing process for 3 weeks, the inotropic compound screening was conducted. The old media was replaced with 90 µL of fresh pre-warmed media the night before compound addition. The cells will were continuously paced for an additional 12 hours at 2 Hz using the CardioECR system. The electrical pacing was terminated 6 hours prior to compound application to ensure that cells generated stable beating rate and beating amplitude for treatment. The cell beating activity is monitored and recorded in real-time on the CardioECR system.

The effective concentration ranges for the test substances were determined. The compound solution is prepared as follows. The compounds are dissolved in the appropriate solvent. If DMSO is used as the solvent, dissolve the compound in a high stock concentration if possible (ideally more than 1000-fold of the highest test concentration) and store at −20° C. Serial dilutions of compounds are prepared 1000× concentrated in appropriate solvent (DMSO or H2O). Diluted compounds are transferred to the wells of a V-bottom microtiter plate for further dilution in culture medium (10× concentrated).

The baseline of beating activity is recorded for 20 seconds every 5 minutes up to 30 minutes immediately prior to compound addition on the CardioECR system. 10 µL of 10× compound solution is added to the wells of CardioECR plate using multichannel pipette. The cell response to the compound is recorded for 20 seconds every 2 minutes immediately after compound exposure using CardioECR system. The cell beating activity, including beating rate and beating amplitude, is evaluated at 30 minutes post compound addition.

As proof of principle, the above assay was conducted using milrinone. As shown in FIG. 7A-B, after exposure to the positive inotropic compound milrinone, beating rate (B) slightly increased in both spontaneous beating cardiomyocytes and chronically paced cardiomyocytes. However, the beating amplitude (A) was significantly increased in electrically paced cardiomyocytes. The data was presented by mean±SD (N=5).

REFERENCES

Batalov I, Feinberg A W. Differentiation of Cardiomyocytes from Human Pluripotent Stem Cells Using Monolayer Culture. *Biomarker Insights*. 2015; 10(Suppl 1):71-76.

Kazutoshi Takahashi, Shinya Yamanaka. Induction of pluripotent stem cells from mouse embryononic and adult fibroblast cultures by defined factors. Cell. 2006; 126: 663-676.

Takahashi K, Tanabe K, Ohnuki M, Narita M, Ichisaka T, Tomoda K, Yamanaka S. Induction of pluripotent stem cells from adult human fibroblasts by defined factors. Cell. 2007 131(5):861-72

Xiuian Yang, Marita Rodriquez, Lil Pabon, Karin A Fischer, Hans Reinecke, Michael Regnier, Nathan J Sniadecki, Hannele Ruohola-Baker, Charles M Murry. Tri-iodo-L-thyronine promotes the maturation of human cardiomyocties-derived from induced pluripotent stem cells. J Mol Cell Cardiol. 2014 July; 72:296-304

Hanna Vourenpaa, Liisa Ikonen, Kirsi Kujala, Outi Huttala, Hertta-Riina Sarkanen, Timo Ylikomi, Katriina Aalto-Setala, Tuula Heinonen. Novel in vitro cardiovascular constructs composed of vascular-like networks and cardiomyocytes. In vitro Cell. Dev. Biol—Animal (2014) 50:275-286

Brustaert D. L. Cardiac endothelial-myocardial signaling: its role in cardiac growth, contractile performance and rhythmicity. 2003 Physiol. Rev. 83:59-115

Lundy S D Z W, Regnier M, Laflamme M. Structural and functional maturation of cardiomyocytes derived from human pluripotent stem cells. Stem Cells Dev. 2013.

Jacot J G, McCulloch A D, Omens J H. Substrate stiffness affects the functional maturation of neonatal rat ventricular myocytes. Biophysical journal. 2008; 95:3479-3487.

Moran A E, Forouzanfar M H, Roth G A, Mensah G A, Ezzati M, Murray C J, Naghavi M Circulation. Temporal trends in ischemic heart disease mortality in 21 world regions, 1980 to 2010: the Global Burden of Disease 2010 study. 2014 Apr. 8; 129(14):1483-92

McDevitt T C, Angello J C, Whitney M L, Reinecke H, Hauschka S D, Murry C E, Stayton P S. In vitro generation of differentiated cardiac myofibers on micropatterned laminin surfaces. Journal of biomedical materials research. 2002; 60:472-479.

Zimmermann W H, Schneiderbanger K, Schubert P, Didie M, Munzel F, Heubach J F, Kostin S, Neuhuber W L, Eschenhagen T. Tissue engineering of a differentiated cardiac muscle construct. Circulation research. 2002; 90:223-230.

Sathaye A, Bursae N, Sheehy S, Tung L. Electrical pacing counteracts intrinsic shortening of action potential duration of neonatal rat ventricular cells in culture. Journal of molecular and cellular cardiology. 2006; 41:633-641.

Christopher A. Werley, Miao-Ping Chien, Jellert Gaublomme, Karthik Shekhar, Vincent Butty, B Alexander Yi, Jole M Kralj, William Bioxham, Lauri A. Boyer, Aviv Regev, Adam E. Cohen. Geometry-dependent functional changes in iPSC-derived cardiomyocytes probed by functional imaging and RNA sequencing.

What is claimed is:

1. A method of maturing functionally immature cardiomyocytes, the method comprising: a) providing a system configured to culture, electrically pace, and monitor beating of beating cells; b) culturing immature cardiomyocytes in the system; c) determining whether or not beating of the immature cardiomyocytes is synchronized by electrically monitoring the immature cardiomyocytes; d) if the beating is not synchronized, electrically pacing the immature cardiomyocyte until the cardiomyocyte beating is synchronized; and e) if the beating is synchronized, electrically pacing the immature cardiomyocytes according to a pulse profile that induces maturation until the immature cardiomyocytes mature into functionally adult cardiomyocytes; wherein the electric pacing in step 1d) is at a different pulse frequency than the electric pacing of step 1e).

2. The method of claim 1, wherein the electric monitoring of the immature cardiomyocytes is by a method selected from the group consisting of monitoring cell-substrate impedance of the immature cardiomyocytes, performing extracellular recording of the immature cardiomyocytes, and both monitoring cell-substrate impedance and performing extracellular recording of the immature cardiomyocytes.

3. The method of claim 1, wherein the pulse profile comprises one or more characteristics selected from the group consisting of a rectangular pulse shape, a pulse intensity of 0.7 V to 1 V, a pulse duration from 0.1 milliseconds to 0.2 milliseconds, and a pulse frequency between 1 Hz and 2 Hz.

4. The method of claim 1, wherein the pulse profile comprises an increasing pulse frequency over time, optionally from 0.75 Hz to 2 Hz.

5. The method of claim 1, wherein the immature cardiomyocytes are paced until displaying a positive beating force-frequency relationship in step e).

* * * * *